US009139670B2

(12) United States Patent
Joly et al.

(10) Patent No.: US 9,139,670 B2
(45) Date of Patent: Sep. 22, 2015

(54) SURFACE-MODIFIED ZIRCONIA NANOPARTICLES

(75) Inventors: Guy D. Joly, Shoreview, MN (US); Nathan E. Schultz, Lakeland, MN (US); Babu N. Gaddam, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 142 days.

(21) Appl. No.: 13/991,578

(22) PCT Filed: Dec. 13, 2011

(86) PCT No.: PCT/US2011/064617
§ 371 (c)(1),
(2), (4) Date: Aug. 19, 2013

(87) PCT Pub. No.: WO2012/087665
PCT Pub. Date: Jun. 28, 2012

(65) Prior Publication Data
US 2013/0338251 A1    Dec. 19, 2013

Related U.S. Application Data

(60) Provisional application No. 61/426,169, filed on Dec. 22, 2010.

(51) Int. Cl.
| | | |
|---|---|---|
| B41J 2/16 | (2006.01) | |
| B29D 11/00 | (2006.01) | |
| C08F 2/46 | (2006.01) | |
| C08G 61/04 | (2006.01) | |
| C08F 22/10 | (2006.01) | |
| B82Y 30/00 | (2011.01) | |
| C01G 25/02 | (2006.01) | |
| C07C 259/06 | (2006.01) | |
| C07C 323/60 | (2006.01) | |
| C09C 1/00 | (2006.01) | |
| C07C 323/52 | (2006.01) | |

(52) U.S. Cl.
CPC ............... *C08F 22/10* (2013.01); *B82Y 30/00* (2013.01); *C01G 25/02* (2013.01); *C07C 259/06* (2013.01); *C07C 323/52* (2013.01); *C07C 323/60* (2013.01); *C09C 1/00* (2013.01); *C01P 2002/54* (2013.01); *C01P 2002/74* (2013.01); *C01P 2002/86* (2013.01); *C01P 2004/64* (2013.01)

(58) Field of Classification Search
CPC ..... C08F 22/10; C07C 323/52; C07C 259/06; C07C 323/60; B22Y 30/00; C01P 2002/54; C01P 2002/86; C01P 2002/74; C01P 2002/64; C09C 1/00; C01G 25/02
USPC ................................... 522/181, 178, 1; 520/1
See application file for complete search history.

(56) References Cited

U.S. PATENT DOCUMENTS

| | | | |
|---|---|---|---|
| 6,376,590 B2 | 4/2002 | Kolb | |
| 6,680,338 B2 | 1/2004 | Montana | |
| 7,156,911 B2 | 1/2007 | Kangas | |
| 7,241,437 B2 | 7/2007 | Davidson | |
| 7,297,810 B2 | 11/2007 | Walker | |
| 7,429,422 B2 | 9/2008 | Davidson | |
| 2006/0084278 A1 | 4/2006 | Winter | |
| 2007/0275042 A1 | 11/2007 | Anderson | |
| 2009/0105437 A1 | 4/2009 | Determan | |
| 2010/0184887 A1 | 7/2010 | Gonzalez | |
| 2010/0227969 A1 | 9/2010 | Zhu | |
| 2011/0126734 A1* | 6/2011 | Joly et al. | 106/287.19 |
| 2011/0288215 A1* | 11/2011 | Shultz et al. | 524/204 |

FOREIGN PATENT DOCUMENTS

| | | | |
|---|---|---|---|
| CN | 101638222 A | 2/2010 | |
| KR | 2007-0022098 | 2/2007 | |
| WO | WO 2007/104312 A2 | 9/2007 | |
| WO | WO 2009-085926 | 7/2009 | |
| WO | WO 2010-085427 | 7/2010 | |
| WO | WO 2010-104645 | 9/2010 | |
| WO | 2010-085427 | * 10/2010 | |
| WO | WO 2011-068697 | 6/2011 | |

OTHER PUBLICATIONS

Folkers, "Self-Assembled Monolayers of Long-Chain Hydroxamic Acids on the Native Oxides of Metals", Langmuir, 1995, vol. 11, No. 3, pp. 813-824.
Lardelli, "The Synthesis of Lactones", Recueil, 1967, vol. 86, pp. 481-503.
International Search Report for PCT International Application No. PCT/US2011/064617, Mailed Jun. 19, 2012, 4 pages.

* cited by examiner

*Primary Examiner* — Ling Choi
*Assistant Examiner* — Jessica E Whiteley
(74) *Attorney, Agent, or Firm* — Qiang Han

(57) ABSTRACT

Surface-modified zirconia nanoparticles include zirconia nanoparticles and surface-modifying ligands attached to the zirconia nanoparticles. The ligand includes a hydroxamate functionality, and either a reactive group or an oligomeric group. Reactive groups include chain transfer groups or photoinitiator groups. Oligomeric groups include poly(meth)acrylate or poly(meth)acrylamide groups. Articles can be prepared that include the surface-modified zirconia nanoparticles in an organic matrix.

18 Claims, No Drawings

SURFACE-MODIFIED ZIRCONIA NANOPARTICLES

FIELD OF THE DISCLOSURE

The present disclosure relates to surface-modified zirconia nanoparticles, ligands for preparing surface-modified zirconia particles, and methods for making and using the same.

BACKGROUND

Zirconia nanoparticles have a high refractive index and are useful in organic matrices to alter optical properties of the matrix. For example, zirconia nanoparticles have been used to increase the index of refraction or to increase the x-ray opacity of the organic matrix, while retaining optical transmission. The extent to which the x-ray opacity and/or refractive index of the organic matrix can be increased is dependent on the percent loading of zirconia in the organic matrix and on characteristics of the zirconia particles such as the percent crystallinity, the crystalline structure, the primary particle size, and the degree of association between the primary particles.

Surface modification of zirconia nanoparticles can be used to prevent or reduce particle agglomeration and to enhance the compatibility of the nanoparticles within an organic matrix. Accordingly, zirconia nanoparticles have been treated with a variety of surface modifying agents such as, for example, carboxylic acids and/or silanes. These traditional surface modifiers have their drawbacks. For example, organic matrices containing acrylic acid-derived residues will displace the zirconia-bound carboxylic acid groups with acrylic acid-derived groups. Silane-functionalized zirconia nanoparticles are thermodynamically unfavorable and experimentally challenging to prepare.

SUMMARY

Disclosed herein are surface-modified zirconia nanoparticles, articles containing surface-modified zirconia nanoparticles, and ligands for surface modification of zirconia nanoparticles. In some embodiments, surface-modified nanoparticles comprise zirconia nanoparticles, and at least one ligand attached to at least one of the zirconia nanoparticles. The ligand comprises a hydroxamate functionality, and a reactive group comprising a chain transfer group or a photoinitiator group. In some embodiments, the chain transfer group comprises a thiol group. In some embodiments, the ligand comprises the structure: $R^1N(OH)(CO)$-A-X, where $R^1$ is selected from a hydrogen atom, an alkyl group, a cycloalkyl group, an aryl group, a heteroaryl group, or a heterocycloalkyl group, (CO) is a carbonyl group C=O, A is a divalent linking group selected from alkylene, arylene, aralkylene, heteroalkylene, heteroarylene, or heteroaralkylene, and X is —SH or —(OC)—O—B—O—Ar—(CO)—C(OH)$R^2{}_2$, where B is an alkylene group or arylene group, Ar is an aryl or substituted aryl group, and each $R^2$ is an alkyl group.

In some embodiments, the surface-modified zirconia nanoparticles comprise oligomeric surface modification groups. The surface-modified zirconia nanoparticles comprise zirconia nanoparticles, and at least one oligomeric ligand attached to at least one of the zirconia nanoparticles. The oligomeric ligand comprises a hydroxamate functionality, and an oligomeric group, where the oligomeric group is formed by the polymerization of free radically polymerizable monomers. The free radically polymerizable monomers comprise a (meth)acrylate, a (meth)acrylamide, a vinylic monomer, a styrenic monomer, an alpha-olefin, or a combination thereof. In some embodiments, the oligomeric ligand comprises the structure: $R^1N(OH)(CO)$-A-Z, where $R^1$ is selected from a hydrogen atom, an alkyl group, a cycloalkyl group, an aryl group, a heteroaryl group, an aralkyl group, a heteroaryl group, or a heterocycloalkyl group, (CO) is a carbonyl group C=O, A is a divalent linking group selected from alkylene, arylene, aralkylene, heteroalkylene, heteroarylene, or heteroaralkylene, and Z is -T-W, where -T- comprises —S— or —(OC)—O—B—O—Ar—(CO)—, where B is an alkylene group or arylene group, and Ar is an aryl or substituted aryl group; and W comprises a poly(meth)acrylate or poly(meth)acrylamide group.

Articles are disclosed herein that comprise a nanoparticle-modified organic matrix. The nanoparticle-modified organic matrix comprises the reaction product of a curable reaction mixture comprising at least one free radically polymerizable monomer, and surface-modified zirconia nanoparticles. The surface-modified zirconia nanoparticles comprise zirconia nanoparticles, and at least one ligand attached to at least one of the zirconia nanoparticles. The ligand comprises a hydroxamate functionality, and a reactive group comprising a chain transfer group or a photoinitiator group. In some embodiments, the curable reaction mixture further comprises an initiator. The free radically polymerizable monomer comprises at least one monomer selected from a (meth)acrylate, a (meth)acrylamide, a vinylic monomer, a styrenic monomer, an alpha-olefin, or a combination thereof. The described articles may be an adhesive, a film, a hardcoat, or a dental composition. In some embodiments, the article is optically clear.

Also disclosed are ligands capable of forming complexes with zirconia nanoparticles. The ligands comprise a hydroxamate functional group, and a reactive group. The reactive group comprises a chain transfer group or a photoinitiator group. In some embodiments, the chain transfer group is a thiol group. In some embodiments, the ligand comprises the structure: $R^1N(OH)(CO)$-A-X, where $R^1$ is selected from a hydrogen atom, an alkyl group, a cycloalkyl group, an aryl group, a heteroaryl group, an aralkyl group, a heteroaryl group, or a heterocycloalkyl group, (CO) is a carbonyl group C=O, A is a difunctional linking group selected from alkylene, arylene, aralkylene, heteroalkylene, heteroarylene, or heteroaralkylene, and X is —(OC)—O—B—O—Ar—(CO)—C(OH)$R^2{}_2$, where B is an alkylene group or arylene group, Ar is an aryl or substituted aryl group, and each $R^2$ is an alkyl group.

DETAILED DESCRIPTION

Zirconia nanoparticles are useful for a wide variety of applications due to, among other properties, their high refractivity and x-ray opacity. Incorporation of zirconia nanoparticles into organic matrices to impart these features to the matrices is very desirable. In order to avoid nanoparticle agglomeration, various surface modification techniques have been used to attach ligands to the surface of the zirconia nanoparticles and thus prevent agglomeration. Many of these surface modification techniques use carboxylic acid functional ligands or alkoxy silane functional ligands. The use of alkoxy silane functional ligands may be disadvantageous because of the relatively long reaction times and elevated temperature processing required to prepare alkoxy silane surface-modified zirconia nanoparticles. The use of carboxylic acid functional ligands may be disadvantageous because in the presence of matrices that contain carboxylic acid groups, the ligands can exchange with carboxylic acid groups of the matrix. This ligand exchange can result in multiple matrix-bound carboxylic acid groups being attached to the zirconia nanoparticle. In this way the zirconia nanoparticle could function as a crosslinking agent for the matrix, making the polymeric matrix difficult to process and detrimentally affecting the properties of the matrix by making it more rigid.

Recently it has been discovered that hydroxamic acids are excellent ligands for zirconia nanoparticles. The PCT Patent Publication WO 2010/085427 (Schultz et al.) describes these ligands, surface-modified zirconia nanoparticles made with them, and matrices that incorporate these surface-modified particles.

The need persists for surface modification ligands for zirconia nanoparticles that give surface-modified zirconia nanoparticles with improved material properties, especially when the zirconia nanoparticles are dispersed in organic matrices. Among these improved material properties are such characteristics as dispersibility, optical properties, hardness, durability, weatherability, and the like. It is desirable for these ligands to strongly and irreversibly attach to zirconia nanoparticles and also be compatible with a variety of organic matrices.

In this disclosure, surface modification ligands for zirconia nanoparticles are disclosed that contain hydroxamic acid complexing groups and also contain either a chain transfer group or a photoinitiator group. These ligands, when complexed with zirconia nanoparticles, provide sites that are reactive with free radical polymerizable monomers. This permits the preparation of zirconia nanoparticles with polymer-functional surface modification ligands. These polymeric ligands have enhanced compatibility since they are the same or similar composition as the surrounding polymer matrix. Additionally, the zirconia nanoparticles can become selectively incorporated into the matrix itself by these free radically co-reactive ligands.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g., 1 to 5 includes 1, 1.5, 2, 2.75, 3, 3.80, 4, and 5) and any range within that range.

As used herein, the term "crystallinity index" refers to the crystalline fraction that is determined by X-ray diffraction analysis.

As used herein, the term "high refractive index" refers to materials that have a real component of refractive index above about 1.47.

As used herein, the term "hydroxamate functionality" refers to at least one hydroxamic acid group and can refer to the protonated hydroxamic acid or deprotonated acid (conjugate base of hydroxamic acid).

As used herein, the terms "(meth)acrylic" and "(meth)acrylate" refer to derivatives of either methacrylic acid or acrylic acid. Similarly, (meth)acrylamide refers to derivatives of either methacrylamide or acrylamide.

As used herein, the term "zirconia" refers to a various stoichiometries for zirconium oxides, most typically $ZrO_2$, and may also be known as zirconium oxide or zirconium dioxide. The zirconia may contain up to 30 weight percent (wt %) of other chemical moieties such as, for example, $Y_2O_3$ and organic material.

The term "adhesive" as used herein refers to polymeric compositions useful to adhere together two adherends. Examples of adhesives are pressure sensitive adhesives.

Pressure sensitive adhesive compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process.

The terms "free radically polymerizable" and "ethylenically unsaturated" are used interchangeably and refer to a reactive group which contains a carbon-carbon double bond which is able to be polymerized via a free radical polymerization mechanism.

Unless otherwise indicated, "optically transparent" refers to an article, film or adhesive that has a high light transmittance over at least a portion of the visible light spectrum (about 400 to about 700 nm). The term "transparent film" refers to a film having a thickness and when the film is disposed on a substrate, an image (disposed on or adjacent to the substrate) is visible through the thickness of the transparent film. In many embodiments, a transparent film allows the image to be seen through the thickness of the film without substantial loss of image clarity. In some embodiments, the transparent film has a matte or glossy finish.

Unless otherwise indicated, "optically clear" refers to an adhesive or article that has a high light transmittance over at least a portion of the visible light spectrum (about 400 to about 700 nm), and that exhibits low haze.

As used herein, the term "polymer" refers to a polymeric material that is a homopolymer or a copolymer. As used herein, the term "homopolymer" refers to a polymeric material that is the reaction product of one monomer. As used herein, the term "copolymer" refers to a polymeric material that is the reaction product of at least two different monomers. As used herein, the term "oligomer" refers to a macromolecule with at least 2 repeat units, typically of lower molecular weight than a polymer.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "aryl" refers to a monovalent group that is carbocyclic and aromatic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "heteroalkylene" refers to a divalent group that includes at least two alkylene groups connected by a thio, oxy, or —NR— where R is alkyl. The heteroalkylene can be linear, branched, cyclic, substituted with alkyl groups, or combinations thereof. Some heteroalkylenes are poloxyyalkylenes where the heteroatom is oxygen such as for example, —$CH_2CH_2(OCH_2CH_2)_nOCH_2CH_2$—.

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The term "heteroarylene" refers to a divalent group that is carbocyclic and aromatic and contains heteroatoms such as sulfur, oxygen, nitrogen or halogens such as fluorine, chlorine, bromine or iodine.

The term "aralkylene" refers to a divalent group of formula —$R^a$—$Ar^a$— where $R^a$ is an alkylene and $Ar^a$ is an arylene (i.e., an alkylene is bonded to an arylene).

In this disclosure, surface-modified zirconia nanoparticles are described. The surface modification is effected through the use of ligands that have hydroxamic acid groups that can complex with the zirconia nanoparticle surface, and also have a reactive group that can react with free radically polymerizable monomers to form zirconia nanoparticles with polymeric surface modifying groups. Because the zirconia nanoparticles have polymeric surface modifying groups they have high compatibility with polymer matrices.

Surface-modified nanoparticles are provided that include zirconia nanoparticles. Zirconia nanoparticles can be obtained from zirconia sols that include a plurality of single crystal zirconia particles. In some embodiments, these particles have an average primary particles size of less than 20 nanometers (nm). These sols can be substantially non-associated and can be highly crystalline exhibiting a crystallinity index of about 0.65 or greater. Of the crystalline phase, about 70% or greater can exist in combined cubic and tetragonal crystal lattice structures without a crystal phase stabilizer. Exemplary zirconia sols can be obtained via a hydrothermal method. Zirconia sols and methods of making the same are described, for example, in U.S. Pat. No. 6,376,590 (Kolb et al.), U.S. Pat. Nos. 7,241,437 and 7,429,422 (both Davidson et al.). The zirconia nanoparticles in sols of these embodiments can contain yttrium in an amount from about 0.1 wt % to 8 wt % based upon the weight of inorganic oxides in the zirconia particles. The particles can be dispersed in an aqueous medium that includes a carboxylic acid such as, for example, formic acid, acetic acid, propionic acid, butyric acid, or a combination thereof.

The zirconia-containing sols are typically clear. The zirconia-containing sols often have a high optical transmission due to the small size and non-associated form of the primary zirconia particles in the sol. High optical transmission of the sol can be desirable in the preparation of transparent or translucent composite materials. As used herein, "optical transmission" refers to the amount of light that passes through a sample (e.g., a zirconia-containing sol) divided by the total amount of light incident upon the sample. The percent optical transmission may be calculated using the equation $$100(I/I_O)$$

where I is the light intensity passing though the sample and $I_O$ is the light intensity incident on the sample. The optical transmission may be determined using an ultraviolet/visible spectrophotometer set at a wavelength of 600 nm with a 1 cm path length. The optical transmission is a function of the amount of zirconia in a sol. For zirconia-containing sols having about 1 wt % zirconia, the optical transmission is typically at least 70%, at least 80 percent, or at least 90%. For zirconia-containing sols having about 10 wt % zirconia, the optical transmission is typically at least 20%, at least 50%, or at least 70%.

The extent of association between the primary particles can be determined from the hydrodynamic particle size. The hydrodynamic particle size can be measured using Photon Correlation Spectroscopy and is described in more detail in PCT Pat. Appl. US 2008/087,385 (Kolb et al.), filed Dec. 12, 2008. The term "hydrodynamic particle size" and "volume-average particle size" are used interchangeably herein. If the particles of zirconia are associated, the hydrodynamic particle size provides a measure of the size of the aggregates and/or agglomerates of primary particles in the zirconia sol. If the particles of zirconia are non-associated, the hydrodynamic particle size provides a measure of the size of the primary particles.

A quantitative measure of the degree of association between the primary particles in the zirconia sol is the dispersion index. As used herein the "dispersion index" is defined as the hydrodynamic particle size divided by the primary particle size. The primary particle size (e.g., the weighted average crystallite size) can be determined using x-ray diffraction techniques and the hydrodynamic particle size (e.g., the volume-average particle size) is determined using Photon Correlation Spectroscopy. As the association between primary particles in the sol decreases, the dispersion index approaches a value of 1 but can be somewhat higher or lower. The zirconia-containing nanoparticles typically have a dispersion index of about 1 to 5, about 1 to 4, about 1 to 3, about 1 to 2.5, or about 1 to 2.

Photon Correlation Spectroscopy can be used to further characterize the zirconia particles in the sol. For example, the intensity of the light scattered by particles is proportional to the sixth power of the particle diameter. Consequently, a light-intensity distribution tends to be more sensitive to larger particles than smaller ones. One type of intensity-based size available from Photo Correlation Spectroscopy is the Z-average Size. It is calculated from the fluctuations in the intensity of scattered light using a cumulants analysis. This analysis also provides a value called the polydispersity index, which is a measure of the breadth of the particle size distribution. The calculations for the Z-average size and Polydispersity Index are defined in the ISO standard document 13321:1996 E.

The zirconia particles tend to have a Z-average size that is no greater than 70 nanometers, no greater than 60 nm, no greater than 50 nm, no greater than 40 nm, no greater than 35 nm, or no greater than 30 nm. The polydispersity index is often less than 0.5, less than 0.4, less than 0.3, less than 0.2, or less than 0.1. A polydispersity index near 0.5 often indicates a broad particle size distribution while a polydispersity index near 0.1 often indicates a narrow particle size distribution.

In addition to the Z-average size and polydispersity index, a complete light-intensity distribution can be obtained during analysis using Photon Correlation Spectroscopy. This can further be combined with the refractive indices of the particles and the refractive index of the suspending medium to calculate a volume distribution for spherical particles. The volume distribution gives the percentage of the total volume of particles corresponding to particles of a given size range. The volume-average size is the size of a particle that corresponds to the mean of the volume distribution. Since the volume of a particle is proportional to the third power of the diameter, this distribution is less sensitive to larger particles than an intensity-based size. That is, the volume-average size will typically be a smaller value than the Z-average size. The zirconia sols typically have a volume-average size that is no greater than 50 nm, no greater than 40 nm, no greater than 30 nm, no greater than 25 nm, no greater than 20 nm, or no greater than 15 nm. The volume-average size is used in the calculation of the dispersion index.

The zirconia-containing nanoparticles can optionally contain yttrium. Any yttrium that is present is typically in the form of yttrium oxide. The presence of yttrium in the zirconia-containing nanoparticle usually facilitates the formation of the cubic/tetragonal phases rather than the monoclinic phase. The cubic and tetragonal phases are often preferred because they tend to have a higher refractive index and x-ray opacity compared to the monoclinic phase. These phases also tend to be more symmetrical, which can be an advantage in some applications when the zirconia-containing nanoparticles are suspended or dispersed in an organic matrix because they have a minimal effect on the viscosity of the organic matrix. Additionally, the percent loading can be higher with the cubic and tetragonal phases.

The mole ratio of yttrium to zirconium (i.e., moles yttrium÷moles zirconium) in the zirconia-containing nanoparticles is often up to 0.25, up to 0.22, up to 0.20, up to 0.16, up to 0.12, up to 0.08. For example, the mole ratio of yttrium to zirconium can be in the range of from 0 to 0.25, from 0 to 0.22, from 0.01 to 0.22, from 0.02 to 0.22, from 0.04 to 0.22, from 0.04 to 0.20, from 0.04 to 0.16, or from 0.04 to 0.12.

Expressed differently as oxides, the zirconia-containing nanoparticles often contain up to 11 mole percent (mol %) $Y_2O_3$ based on the moles of the inorganic oxides (i.e., $Y_2O_3$ plus $ZrO_2$). For example, the zirconia-containing nanoparticles can contain up to 10 mole percent, up to 8 mole percent, up to 6 mol %, or up to 4 mol % $Y_2O_3$ based on the moles of the inorganic oxides. Some zirconia-containing nanoparticles contain from 0 to 11 mol %, from 0 to 10 mol %, from 1 to 10 mol %, from 1 to 8 mol %, or from 2 to 8 mol % $Y_2O_3$ based on the moles of the inorganic oxides.

Expressed in yet another manner, the zirconia-containing nanoparticles often contain up to 20 weight percent (wt %) $Y_2O_3$ based on the weight of the inorganic oxides (i.e., $Y_2O_3$ plus $ZrO_2$). For example, the zirconia-containing nanoparticles can contain up to 18 wt %, up to 16 wt %, up to 12 wt %, up to 10 wt %, or up to 6 wt % $Y_2O_3$ based on the weight of the inorganic oxides. Some zirconia-containing nanoparticles contain from 0 to 20 wt %, from 0 to 18 wt %, from 2 to 18 wt %, from 2 to 16 wt %, or from 2 to 10 wt % $Y_2O_3$ based on the weight of the inorganic oxides.

The zirconia-containing nanoparticles often contain at least some organic material in addition to inorganic oxides. The organic material can be attached to the surface of the zirconia particles and often originates from the carboxylate species (anion, acid, or both) included in the feedstock or formed as a byproduct of the hydrolysis and condensation reactions. That is, the organic material is often sorbed to the surface of the zirconia-containing nanoparticles. The zirconia particles often contain up to 15 wt %, up to 12 wt %, up to 10 wt %, up to 8 wt %, or up to 6 wt % organic material based on the weight of the particles.

The zirconia-containing nanoparticles often contain less than 3 milligrams of an alkali metal such as sodium, potassium, or lithium per gram of zirconium in the nanoparticles. For example, the amount of alkali metal can be less than 2 milligrams (mg) per gram of zirconium, less than 1 mg per gram of zirconium, less than 0.6 mg per gram of zirconium, less than 0.5 mg per gram of zirconium, less than 0.3 mg per gram of mg, less than 0.2 mg per gram of zirconium, or less than 0.1 mg per gram of zirconium.

Likewise, the zirconia-containing nanoparticles often contain less than 3 mg of an alkaline earth such as calcium, magnesium, barium, or strontium per gram of zirconium in the nanoparticles. For example, the amount of alkaline earth can be less than 2 mg per gram of zirconium, less than 1 mg per gram of zirconium, less than 0.6 mg per gram of zirconium, less than 0.5 mg per gram of zirconium, less than 0.3 mg per gram of zirconium, less than 0.2 mg per gram of zirconium, or less than 0.1 mg per gram of zirconium.

The zirconia-containing nanoparticles can be substantially crystalline. Crystalline zirconia tends to have a higher refractive index and higher x-ray scattering capability than amorphous zirconia. Due to the difficulty in separately quantifying cubic and tetragonal crystal structures for small particles using x-ray diffraction (i.e., the (111) peak for cubic zirconia often overlaps with the (101) peak for tetragonal zirconia). If yttrium is present, at least 70% of the total peak area of the x-ray diffraction scan is attributed to a cubic structure, tetragonal structure, or a combination thereof with the balance being monoclinic. For example, at least 75%, at least 80%, or at least 85% of the total peak area of some x-ray diffraction scans can be attributed to a cubic crystal structure, tetragonal crystal structure, or a combination thereof. Cubic and tetragonal crystal structures tend to promote the formation of low aspect ratio primary particles having a cube-like shape when viewed under an electron microscope.

The zirconia particles usually have an average primary particle size no greater than 50 nm, no greater than 40 nm, no greater than 30 nm, no greater than 25 nm, no greater than 20 nm, no greater than 15 nm, or no greater than 10 nm. The primary particle size, which refers to the non-associated particle size of the zirconia particles, can be determined by x-ray diffraction.

Nanoparticles, such as zirconia nanoparticles, typically agglomerate and it can be difficult to achieve good dispersions of them in media, such as aqueous or organic media. In particular, it can be difficult to get dispersed nanoparticles within a polymer matrix due to the tendency of the nanoparticles to associate into agglomerates. Therefore, it can be advantageous to modify the surface of the nanoparticles so that agglomeration is prevented or inhibited. Surface modification involves reacting the zirconia particles with a surface modification agent or combination of surface modification agents that attach to the surface of the zirconia nanoparticles and that modify the surface characteristics of the zirconia particles.

The surface-modified nanoparticles of this disclosure comprise zirconia nanoparticles with at least one ligand attached to at least one of the zirconia nanoparticles. The ligand has a hydroxamate functionality, and a reactive group comprising a chain transfer group such as a thiol group or a photoinitiator group. The ligands will be described in greater detail below.

The surface modification ligands can be represented by the general Formula 1:

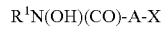   Formula 1

In Formula 1: $R^1$ is selected from a hydrogen atom, an alkyl group, a cycloalkyl group, an aryl group, a heteroaryl group, an aralkyl group, a heteroaryl group, or a heterocycloalkyl group; (CO) is a carbonyl group C=O; A is a difunctional linking group selected from alkylene, arylene, aralkylene, heteroalkylene, heteroarylene, or heteroaralkylene; and X is —SH or —(OC)—O—B—O—Ar—(CO)—C(OH)$R^2_2$ where B is an alkylene group or arylene group; Ar is an aryl or substituted aryl group; and each $R^2$ is an alkyl group.

In some embodiments, the ligand is a chain transfer group. One particularly suitable example is a thiol-functional ligand, where X is —SH. In some of these embodiments, $R^1$ is a hydrogen atom. In some embodiments, the A group of Formula 1 is an alkylene group with 1-10 carbon atoms or a branched heteroalkylene group with the structure: —$CR^4R^5$—$(CH_2CH_2)_n$— where $R^4$ is H, $R^5$ is —(NH(CO)—$CH_3$), and n is an integer of 1 or greater. In one particularly desirable embodiment, the A group is a propylene group. In another particularly desirable embodiment, the A group is a heteroalkylene group with the structure: —$CR^4R^5$—$(CH_2CH_2)_n$—, wherein $R^4$ is a hydrogen atom, $R^5$ is the group —(NH(CO)—$CH_3$); and n is 1.

In some embodiments, the ligand is a photoinitiator-functional ligand, where X is —(OC)—O—B—O—Ar—(CO)—$C(OH)R^2_2$, where B is an alkylene group with 1-10 carbon atoms; Ar is a phenylene group; each $R^2$ is an alkyl group with 1-5 carbon atoms; and A is an alkylene group with 1-10 carbon atoms. In some of these embodiments, $R^1$ is a hydrogen atom. In one particularly desirable embodiment, the B group is an ethylene group, each $R^2$ is a methyl group; and A is a propylene group.

The hydroxamic acid group of the ligands is capable of complexing with the zirconia nanoparticle surface. Hydroxamic acids are a well-studied class of compounds. They are known to form self-assembled monolayers on native oxides of metals as described by J. P. Folkers, et al., "Self-Assembled Monolayers of Long-Chain Hydroxamic Acids on Native Oxides of Metals," *Langmuir*, 11, 813 (1998). Hydroxamic acids have been used in medicinal chemistry applications. The biological activity of hydroxamic acids is due to their strong metal-binding capabilities. For example, hydroxamic acids have been used to treat patients with an excessive concentration of iron in their bloodstream. In addition, hydroxamic acids can inhibit many enzymes including proteases, ureases, oxygenases, hydrolases, and peroxidases and can provide antibacterial, antifungal, and insecticidal protection for plants.

Hydroxamic acids can be obtained commercially from a number of chemical suppliers such as, for example, Sigma Aldrich, St. Louis, Mo. Synthetically, hydroxamic acids can be obtained by reaction between a hydroxylamine and a carbonyl-based electrophile, such as an acid chloride. Coupling reactions between a hydroxylamine and a carboxylic acid can be carried out directly using coupling and/or activating agents that are useful in the synthesis of amides. These agents include, for example, carbodiimides. Aldehydes can be reacted with sulfonamides such as N-hydroxybenzenesulfonamide in the presence of base to form hydroxamic acids. Alternatively, hydroxamic acids can be generated from esters and hydroxylamine reagents. Lactones can make good starting materials for directly generating hydroxyl-functionalized hydroxamic acids. This synthetic pathway is described, for example, by G. Lardelli, et al., *Recueil des Travaux Chimiques des Pays-Bas*, 86, 481-503 (1967). Other useful hydroxamic acids can be found, for example, in U.S. Pat. No. 6,680,338 (Montana et al).

The reactive group, X, comprises either a chain transfer group or a photoinitiator group. Each of these reactive groups provide a site for reaction with free radically polymerizable monomers, and thus a site where a polymer chain can grow. An example of a chain transfer group is a thiol group, as thiol groups are known to function as chain transfer agents. In chain transfer, a free radical on a growing polymer chain reacts with the —SH group. The hydrogen atom caps the growing polymer chain, stopping the growth of the polymer chain and creating a sulfur-based free radical. This sulfur-based free radical can then react with the free radically polymerizable monomers to begin growing a new polymer chain. Therefore, when present in a mixture of free radically polymerizable monomers that are polymerizing, the thiol reactive groups will cause chain transfer and a polymer chain will grow from the formed sulfur-based free radical site.

Similarly, the photoinitiator group will, upon initiation, generate a free radical. The free radical, when in the presence of free radically polymerizable monomers will grow a polymer chain from the site of initiation.

The amount of surface modification ligand used to surface-modify the zirconia nanoparticles may vary dependent upon a variety of factors such as the desired use for the surface-modified zirconia nanoparticles, the nature of the specific ligands used, etc. The amount should be sufficient to prevent agglomeration of the zirconia nanoparticles. In some embodiments, the total amount of added surface-modifying ligand is in the range of 0.5-1.9 mmoles of ligand per dry gram of zirconia nanoparticles. In some embodiments, the total amount of added surface-modifying ligand is in the range of 0.9-1.5 mmoles of ligand per dry gram of zirconia nanoparticles, or even about 1.4 mmoles of ligand per dry gram of zirconia nanoparticles.

In some embodiments, the surface-modified nanoparticles comprises at least one additional ligand with a hydroxamate functionality. These additional ligands do not contain reactive groups, but they contain groups that aid the compatibility of the surface-modified zirconia nanoparticles with polymeric matrices and also help to prevent agglomeration of the zirconia nanoparticles.

Examples of suitable additional ligands are the hydroxamate ligands described in the PCT Patent Publication WO 2010/085427 (Schultz et al.). Suitable additional ligands are of the general structure of Formula 2:

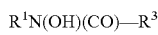  Formula 2

In Formula 2: $R^1$ is selected from a hydrogen atom, an alkyl group, a cycloalkyl group, an aryl group, a heteroaryl group, an aralkyl group, a heteroaryl group, or a heterocycloalkyl group; (CO) is a carbonyl group C=O; and $R^3$ is an alkyl group, a cycloalkyl group, an aryl group, a heteroaryl group, an aralkyl group, a heteroaryl group, or a heterocycloalkyl group.

Whether additional ligands are used in addition to the reactive ligands described above depends upon a variety of factors including cost factors as well as the desired physical characteristics of the surface-modified zirconia nanoparticles. Similarly, when the additional ligands are used, the amount of additional ligands used will vary. The amount of additional ligands used is in the range of 0-99 mole % based upon the total moles of ligands used. Typically the amount of additional ligands used is less than 95 mole %, or less than 90 mole % of the total moles of ligands used. More typically, less than 50 mole %, less than 40 mole %, or even about 25 mole % or less of additional ligands are used.

Also disclosed are surface-modified zirconia nanoparticles comprising zirconia nanoparticles, and at least one polymeric ligand attached to at least one of the zirconia nanoparticles. The polymeric ligand comprises a hydroxamate functionality, and an oligomeric group. The oligomeric group is formed by polymerizing free radically polymerizable monomers. In some embodiments, the oligomeric group comprises a (meth)acrylate or (meth)acrylamide oligomer.

The zirconia nanoparticles with polymeric ligands attached are prepared from the zirconia nanoparticles with ligands containing reactive groups. Depending upon which ligands containing reactive groups are present, different techniques can be employed to generate zirconia nanoparticles with polymeric ligands.

When the zirconia nanoparticles have ligands with thiol groups, the zirconia nanoparticles with ligands containing thiol groups are mixed with free radically polymerizable monomers. Examples of free radically polymerizable monomers include (meth)acrylate monomers, (meth)acrylamide monomers, vinyl monomers, styrenic monomers, alpha-olefinic monomers, and the like. Particularly suitable monomers are (meth)acrylate and (meth)acrylamide monomers. When the free radically polymerizable monomers are polymerized, the thiol groups act as chain transfer agents and oligomeric groups grow from the sulfur atom of the thiol group. In some embodiments, the oligomeric groups comprise (meth)acrylate or (meth)acrylamide oligomeric groups. The zirconia nanoparticles with ligands containing polymeric groups are formed as a polymeric matrix forms around the nanoparticles.

When the zirconia nanoparticles have ligands with photoinitiator groups, the zirconia nanoparticles with ligands containing photoinitiator groups are mixed with free radically polymerizable monomers. Suitable free radically polymerizable monomers are described above. Particularly suitable monomers are (meth)acrylate and (meth)acrylamide monomers. When the photoinitiator group is exposed to actinic radiation, a free radical is generated on the ligands attached to the zirconia nanoparticles, and polymeric groups grow from the ligands. Because the polymeric groups are initiated by the ligand, zirconia nanoparticles with polymeric ligands can be prepared without forming a polymeric matrix around the nanoparticles. In this way, zirconia nanoparticles with polymeric ligands can be isolated. The isolated nanoparticles with polymeric ligands can be subsequently mixed with free radically polymerizable monomers or a pre-formed polymeric matrix. Additionally, as with the zirconia nanoparticles that have thiol reactive groups, the zirconia nanoparticles with ligands containing polymeric groups can be formed as a polymeric matrix forms around the nanoparticles.

The polymeric ligand comprises the general structure of Formula 3:

$$R^1N(OH)(CO)\text{-}A\text{-}Z \qquad \text{Formula 3}$$

In Formula 3: $R^1$ is selected from a hydrogen atom, an alkyl group, a cycloalkyl group, an aryl group, a heteroaryl group, an aralkyl group, a heteroaryl group, or a heterocycloalkyl group; (CO) is a carbonyl group C=O; A is a divalent linking group selected from alkylene, arylene, aralkylene, heteroalkylene, heteroarylene, or heteroaralkylene; and Z is -T-W where T comprises —S— or —(OC)—O—B—O—Ar—(CO)—, wherein B is an alkylene group or arylene group; and Ar is an aryl or substituted aryl group, and W comprises an oligomeric group formed by polymerization of free radically polymerizable monomers. In some embodiments, W comprises a poly(meth)acrylate or poly(meth)acrylamide oligomeric group.

In some embodiments, the surface-modified nanoparticles with polymeric ligands comprise at least one additional ligand with a hydroxamate functionality. These additional ligands are described above by Formula 2 and suitable amounts of such ligands are also described above.

To make surface-modified zirconia nanoparticles, an aqueous sol of acetate-functionalized zirconia nanoparticles is provided as described above. A solution is mixed with the sol that includes at least one ligand with hydroxamate functionality and a reactive group, where the reactive group comprises a chain transfer group or a photoinitiator group. The mixture is then, optionally, heated and water and displaced acetic acid is removed from the mixture to form surface-modified zirconia nanoparticles that can be isolated as a powder or slurry.

Also disclosed herein are zirconia nanoparticle-modified polymeric matrices. As described above, in some embodiments, zirconia nanoparticles with polymeric ligands can be prepared and isolated. These zirconia nanoparticles with polymeric ligands can be mixed with free radically polymerizable monomers, and upon polymerization of the monomers the zirconia nanoparticle-modified polymeric matrix can be formed. Examples of suitable free radically polymerizable monomers include (meth)acrylate monomers, (meth)acrylamide monomers, vinyl monomers, styrenic monomers, alpha-olefinic monomers, and the like. Particularly suitable monomers are (meth)acrylate and (meth)acrylamide monomers. Additionally, the zirconia nanoparticles with polymeric ligands can be mixed with a pre-formed polymeric matrix to generate the zirconia nanoparticle-modified polymeric matrix. Examples of suitable pre-formed polymeric matrices include, for example, poly(meth)acrylates, poly(meth)acrylamides, polyolefins, polyesters, polyethers, polyurethanes, polyepoxides, polyimides, polyamides, polycarbonates, and the like.

In other embodiments, zirconia nanoparticle-modified polymeric matrices are prepared by preparing a curable reaction mixture. The curable reaction mixture is prepared by mixing surface-modified zirconia nanoparticles containing ligands with reactive groups with at least one free radically polymerizable monomer. Examples of suitable free radically polymerizable monomers include (meth)acrylate monomers, (meth)acrylamide monomers, vinyl monomers, styrenic monomers, alpha-olefinic monomers, and the like. Particularly suitable monomers are (meth)acrylate and (meth)acrylamide monomers. As described above, the ligands with reactive groups may have chain transfer groups or photoinitiator groups. When the free radically polymerizable monomers are polymerized, polymeric ligands are formed on the zirconia nanoparticles as the matrix forms. Because the polymeric ligands and the matrix are formed simultaneously and from the same monomers, the nanoparticles have a high compatibility with the polymeric matrix.

In addition, the curable reaction mixture typically includes either a thermal initiator or a photoinitiator. Examples of thermal initiators include peroxides such as benzoyl peroxide and its derivatives or azo compounds such as VAZO 67, available from E. I. du Pont de Nemours and Co. Wilmington, Del., which is 2,2'-azobis-(2-methylbutyronitrile), or V-601, available from Wako Specialty Chemicals, Richmond, Va., which is dimethyl-2,2'-azobisisobutyrate. A variety of peroxide or azo compounds are available that can be used to initiate thermal polymerization at a wide variety of temperatures. The precursor mixtures can include a photoinitiator. Particularly useful are initiators such as IRGACURE 651 (2,2-dimethoxy-2-phenylacetophenone) or IRGACURE 2959 (1-[4-(2-hydroxyethoxy)-phenyl]-2-hydroxy-2-methyl-1-propane-1-one), available from Ciba Chemicals, Tarrytown, N.Y. Typically, the crosslinker, if present, is added to the precursor mixtures in an amount of from about 0.05 parts by weight to about 5.00 parts by weight based upon the other constituents in the mixture. The initiators are typically added to the precursor mixtures in the amount of from 0.05 parts by weight to about 2 parts by weight. The precursor mixtures can be polymerized and/or cross-linked using actinic radiation or heat to form the adhesive composition as described above and in the Examples below.

The zirconia nanoparticle-modified polymeric matrices of this disclosure may comprise a wide variety of articles. Examples of articles include adhesives, films, hardcoats, and dental composites. Films include a wide range of optical films including optical composite films.

In some embodiments, the organic matrix can be an adhesive composition. Typically the adhesive compositions can be (meth)acrylic pressure sensitive adhesives. The adhesive compositions can be derived from precursors that include from about 75 to about 99 parts by weight of an alkyl acrylate having 1 to 14 carbons in the alkyl group. The alkyl acrylate can include aliphatic, cycloaliphatic, or aromatic alkyl groups. Useful alkyl acrylates (i.e., acrylic acid alkyl ester monomers) include linear or branched monofunctional acrylates or methacrylates of non-tertiary alkyl alcohols, the alkyl groups of which have from 1 up to 14 and, in particular, from 1 up to 12 carbon atoms. Useful monomers include, for example, 2-ethylhexyl (meth)acrylate, ethyl (meth)acrylate, methyl (meth)acrylate, n-propyl (meth)acrylate, isopropyl (meth)acrylate, pentyl (meth)acrylate, n-octyl (meth)acrylate, isooctyl (meth)acrylate, isononyl (meth)acrylate, n-butyl (meth)acrylate, isobutyl (meth)acrylate, hexyl (meth)acrylate, n-nonyl (meth)acrylate, iso amyl (meth)acrylate, n-decyl (meth)acrylate, isodecyl (meth)acrylate, dodecyl (meth)acrylate, isobornyl (meth)acrylate, cyclohexyl (meth)acrylate, phenyl meth(acrylate), benzyl meth(acrylate), and 2-methylbutyl (meth)acrylate, biphenyloxyethyl acrylate (BPEA), 6-(2-biphenoxy)hexyl acrylate, and combinations thereof.

The provided adhesive composition precursors can also include from about 1 to about 25 parts of a copolymerizable polar monomer such as (meth)acrylic monomer containing carboxylic acid, amide, urethane, or urea functional groups. Useful carboxylic acids include acrylic acid and methacrylic acid. Weak polar monomers like N-vinyl lactams may also be included. A useful N-vinyl lactam is N-vinyl caprolactam. In general, the polar monomer content in the adhesive can include less than about 10 parts by weight or even less than about 5 parts by weight of one or more polar monomers. Useful amides include N-vinyl caprolactam, N-vinyl pyrrolidone, (meth)acrylamide, N-methyl (meth)acrylamide, N,N-dimethyl acrylamide, N,N-dimethyl meth(acrylamide), and N-octyl (meth)acrylamide.

The pressure sensitive adhesive can be inherently tacky. If desired, tackifiers can be added to the precursor mixture before formation of the pressure sensitive adhesive or can be added to the polymerized matrix. Useful tackifiers include, for example, rosin ester resins, aromatic hydrocarbon resins, aliphatic hydrocarbon resins, and terpene resins. In general, light-colored tackifiers selected from hydrogenated rosin esters, terpenes, or aromatic hydrocarbon resins can be used.

Other materials can be added for special purposes, including, for example, oils, plasticizers, antioxidants, UV stabilizers, pigments, curing agents, polymer additives, and other additives provided that they do not significantly reduce the optical clarity of the pressure sensitive adhesive.

The provided adhesive compositions (that include surface-modified zirconia nanoparticles) may have additional components added to the precursor mixture. For example, the mixture may include a multifunctional crosslinker. Such crosslinkers include thermal crosslinkers which are activated during the drying step of preparing solvent coated adhesives and crosslinkers that copolymerize during the polymerization step. Such thermal crosslinkers may include multifunctional isocyanates, aziridines, multifunctional (meth)acrylates, and epoxy compounds. Exemplary crosslinkers include difunctional acrylates such as 1,6-hexanediol diacrylate or multi-functional acrylates such as are known to those of skill in the art. Useful isocyanate crosslinkers include, for example, an aromatic diisocyanate available as DESMODUR L-75 from Bayer, Cologne, Germany. Ultraviolet, or "UV", activated crosslinkers can also be used to crosslink the pressure sensitive adhesive. Such UV crosslinkers may include benzophenones and 4-acryloxybenzophenones.

The pressure sensitive adhesive precursors can be blended with the provided surface-modified zirconia nanoparticles to form an optically transparent or translucent mixture. Typically, the mixtures can contain up to about 25 wt % zirconia or even more. The mixture can be polymerized by exposure to heat or actinic radiation (to decompose initiators in the mixture). This can be done prior to the addition of a cross-linker to form a coatable syrup to which, subsequently, one or more crosslinkers, and optionally additional initiators can be added, the syrup can be coated on a liner, and cured (i.e., cross-linked) by an addition exposure to initiating conditions for the added initiators. Alternatively, the crosslinker and initiators can be added to the monomer mixture and the monomer mixture can be both polymerized and cured in one step. The desired coating viscosity can determine which procedure is used. The disclosed adhesive compositions or precursors may be coated by any variety of known coating techniques such as roll coating, spray coating, knife coating, die coating, and the like. Alternatively, the adhesive precursor composition may also be delivered as a liquid to fill the gap between the two substrates and subsequently be exposed to heat or UV to polymerize and cure the composition. The thickness of the adhesive layer in the articles of disclosure tends to be greater than about 5 micrometers (μm), greater than about 10 μm, greater than about 15 μm, or even greater than about 20 μm. The thickness is often less than about 1000 μm, less than about 250 μm, less than about 200 μm, or even less than about 175 μm. For example, the thickness can be from about 5 to about 1000 μm, from about 10 to about 500 μm, from about 25 to about 250 μm, or from about 50 to about 175 μm.

In some embodiments, the organic matrix can be a film or hardcoat composition. Many film or hardcoat articles thus formed are optical articles. In some embodiments, surface-modified zirconia nanoparticles can be dispersed and bonded into optically clear organic matrices to produce high refractive index composites. These high index films or hardcoats can be useful to make optical display elements or other optical elements that have low reflection (for example, anti-reflective properties).

In some embodiments, compositions that include surface-modified zirconia nanoparticles can be radioopaque. By radioopaque it is meant that the compositions absorb or scatter X-ray radiation. These materials can be useful, for example, in dental or medical applications.

The present disclosure includes the following embodiments.

Among the embodiments are surface-modified zirconia nanoparticles. A first embodiment includes surface-modified nanoparticles comprising: zirconia nanoparticles; and at least one ligand attached to at least one of the zirconia nanoparticles, the ligand comprising: a hydroxamate functionality; and a reactive group comprising a chain transfer group or a photoinitiator group.

Embodiment 2 is the surface-modified nanoparticles of embodiment 1, wherein the chain transfer group comprises a thiol group.

Embodiment 3 is the surface-modified nanoparticles of embodiment 1 or 2, wherein the ligand comprises the structure: $R^1N(OH)(CO)$-A-X wherein $R^1$ is selected from a hydrogen atom, an alkyl group, a cycloalkyl group, an aryl group, a heteroaryl group, an aralkyl group, a heteroaryl group, or a heterocycloalkyl group; (CO) is a carbonyl group C=O; A is a divalent linking group selected from alkylene, arylene, aralkylene, heteroalkylene, heteroarylene, or heteroaralkylene; and X is —SH or —(OC)—O—B—O—Ar—(CO)—C(OH)$R^2_2$ wherein B is an alkylene group or arylene group; Ar is an aryl or substituted aryl group; and each $R^2$ is an alkyl group.

Embodiment 4 is the surface-modified nanoparticles of any of embodiments 1-3, further comprising at least one additional ligand comprising a hydroxamate functionality.

Embodiment 5 is the surface-modified nanoparticles of embodiment 4, wherein the at least one additional ligand comprises the structure: $R^1$N(OH)(CO)—$R^3$ wherein $R^1$ is selected from a hydrogen atom, an alkyl group, a cycloalkyl group, an aryl group, a heteroaryl group, an aralkyl group, a heteroaryl group, or a heterocycloalkyl group; (CO) is a carbonyl group C=O; and $R^3$ is an alkyl group, a cycloalkyl group, an aryl group, a heteroaryl group, an aralkyl group, a heteroaryl group, or a heterocycloalkyl group.

Embodiment 6 is the surface-modified nanoparticles of embodiment 5, wherein $R^3$ is a polar or non-polar compatibilizing group.

Embodiment 7 is the surface-modified nanoparticles of embodiment 6, wherein the polar compatibilizing group, if present, is selected from a hydroxyl group, a carboxylic acid group, an amine group, a thiol, an epoxide, an aziridine, an azide, a halide, an alkyne, an olefin, or a combination thereof.

Embodiment 8 is the surface-modified nanoparticles of embodiment 6, wherein the non-polar compatibilizing group, if present, is selected from alkyl, alkylene, heteroalkyl, aryl, arylene, or combinations thereof.

Embodiment 9 is the surface-modified nanoparticles of any of embodiments 4-8, wherein the at least one additional ligand comprises up to 99% by moles of the total ligands.

Embodiment 10 is the surface-modified nanoparticles of any of embodiments 4-9, wherein the at least one additional ligand comprises up to 95% by moles of the total ligands.

Embodiment 11 is the surface-modified nanoparticles of any of embodiments 4-10, wherein the at least one additional ligand comprises up to 90% by moles of the total ligands.

Embodiment 12 is the surface-modified nanoparticles of any of embodiments 4-11, wherein the at least one additional ligand comprises up to 50% by moles of the total ligands.

Embodiment 13 is the surface-modified nanoparticles of any of embodiments 4-12, wherein the at least one additional ligand comprises up to 40% by moles of the total ligands.

Embodiment 14 is the surface-modified nanoparticles of any of embodiments 4-13, wherein the at least one additional ligand comprises up to 25% by moles of the total ligands.

Also included are embodiments of surface-modified zirconia nanoparticles comprising oligomeric ligands. Embodiment 15 includes surface-modified nanoparticles comprising: zirconia nanoparticles; and at least one oligomeric ligand attached to at least one of the zirconia nanoparticles, the oligomeric ligand comprising: a hydroxamate functionality; and an oligomeric group, wherein the oligomeric group is formed by the polymerization of free radically polymerizable monomers.

Embodiment 16 is the surface-modified nanoparticles of embodiment 15, wherein the free radically polymerizable monomers comprise a (meth)acrylate, a (meth)acrylamide, a vinylic monomer, a styrenic monomer, an alpha-olefin, or a combination thereof.

Embodiment 17 is the surface-modified nanoparticles of embodiment 15 or 16, wherein the oligomeric ligand comprises the structure: $R^1$N(OH)(CO)-A-Z wherein $R^1$ is selected from a hydrogen atom, an alkyl group, a cycloalkyl group, an aryl group, a heteroaryl group, an aralkyl group, a heteroaryl group, or a heterocycloalkyl group; (CO) is a carbonyl group C=O; A is a divalent linking group selected from alkylene, arylene, aralkylene, heteroalkylene, heteroarylene, or heteroaralkylene; and Z is -T-W wherein -T- comprises —S— or —(OC)—O—B—O—Ar—(CO)—, wherein B is an alkylene group or arylene group; and Ar is an aryl or substituted aryl group; and W comprises a poly(meth)acrylate or poly(meth)acrylamide group.

Embodiment 18 is the surface-modified nanoparticles of any of embodiments 15-17, further comprising at least one additional ligand comprising a hydroxamate functionality.

Embodiment 19 is the surface-modified nanoparticles of embodiment 18, wherein the at least one additional ligand comprises the structure: $R^1$N(OH)(CO)—$R^3$ wherein $R^1$ is selected from a hydrogen atom, an alkyl group, a cycloalkyl group, an aryl group, a heteroaryl group, an aralkyl group, a heteroaryl group, or a heterocycloalkyl group; (CO) is a carbonyl group C=O; and $R^3$ is an alkyl group, a cycloalkyl group, an aryl group, a heteroaryl group, an aralkyl group, a heteroaryl group, or a heterocycloalkyl group.

Embodiment 20 is the surface-modified nanoparticles of embodiment 18 or 19, wherein $R^3$ is a polar or non-polar compatibilizing group.

Embodiment 21 is the surface-modified nanoparticles of embodiment 20, wherein the polar compatibilizing group, if present, is selected from a hydroxyl group, a carboxylic acid group, an amine group, a thiol, an epoxide, an aziridine, an azide, a halide, an alkyne, an olefin, or a combination thereof.

Embodiment 22 is the surface-modified nanoparticles of embodiment 20, wherein the non-polar compatibilizing group, if present, is selected from alkyl, alkylene, heteroalkyl, aryl, arylene, or combinations thereof.

Embodiment 23 is the surface-modified nanoparticles of any of embodiments 18-22, wherein the at least one additional ligand comprises up to 99% by moles of the total ligands.

Embodiment 24 is the surface-modified nanoparticles of any of embodiments 18-23, wherein the at least one additional ligand comprises up to 95% by moles of the total ligands.

Embodiment 25 is the surface-modified nanoparticles of any of embodiments 18-24, wherein the at least one additional ligand comprises up to 90% by moles of the total ligands.

Embodiment 26 is the surface-modified nanoparticles of any of embodiments 18-25, wherein the at least one additional ligand comprises up to 50% by moles of the total ligands.

Embodiment 27 is the surface-modified nanoparticles of any of embodiments 18-26, wherein the at least one additional ligand comprises up to 40% by moles of the total ligands.

Embodiment 28 is the surface-modified nanoparticles of any of embodiments 18-27, wherein the at least one additional ligand comprises up to 25% by moles of the total ligands.

Also included are embodiments of articles. Embodiment 29 includes an article comprising: a nanoparticle-modified organic matrix, the nanoparticle-modified organic matrix comprising the reaction product of a curable reaction mixture comprising: at least one free radically polymerizable monomer; and surface-modified zirconia nanoparticles, wherein the surface-modified zirconia nanoparticles comprise: zirconia nanoparticles; and at least one ligand attached to at least one of the zirconia nanoparticles, the ligand comprising: a hydroxamate functionality; and a reactive group comprising a chain transfer group or a photoinitiator group.

Embodiment 30 is the article of embodiment 29, wherein the curable reaction mixture further comprises an initiator.

Embodiment 31 is the article of embodiment 29 or 30, wherein the free radically polymerizable monomer comprises at least one monomer selected from a (meth)acrylate, a (meth) acrylamide, a vinylic monomer, a styrenic monomer, an alpha-olefin, or a combination thereof.

Embodiment 32 is the article of any of embodiments 29-31, wherein the article comprises an adhesive, a film, a hardcoat, or a dental composition.

Embodiment 33 is the article of any of embodiments 29-32, wherein the article is optically clear.

Also included are embodiments of ligands capable of complexing zirconia nanoparticles. Embodiment 34 includes a ligand comprising: a hydroxamate functional group; and a reactive group comprising a chain transfer group or a photoinitiator group.

Embodiment 35 is the ligand of embodiment 34, wherein the chain transfer group comprises a thiol group.

Embodiment 36 is the ligand of embodiment 34 comprising the structure: $R^1N(OH)(CO)$-A-X, wherein $R^1$ is selected from a hydrogen atom, an alkyl group, a cycloalkyl group, an aryl group, a heteroaryl group, an aralkyl group, a heteroaryl group, or a heterocycloalkyl group; (CO) is a carbonyl group C=O; A is a difunctional linking group selected from alkylene, arylene, aralkylene, heteroalkylene, heteroarylene, or heteroaralkylene; and X is —SH or —(OC)—O—B—O—Ar—(CO)—C(OH)$R^2_2$ wherein B is an alkylene group or arylene group; Ar is an aryl or substituted aryl group; and each $R^2$ is an alkyl group.

Embodiment 37 is the ligand of embodiment 36, wherein $R^1$ is H; X is —SH; and A is an alkylene group with 1-10 carbon atoms or a branched heteroalkylene group with the structure: —$CR^4R^5$—$(CH_2CH_2)_n$— wherein $R^4$ is H; $R^5$ is —(NH(CO)—$CH_3$); and n is an integer of 1 or greater.

Embodiment 38 is the ligand of embodiment 36, wherein A is an propylene group.

Embodiment 39 is the ligand of embodiment 36, wherein A is heteroalkylene group with the structure: —$CR^4R^5$—$(CH_2CH_2)_n$— wherein $R^4$ is H; $R^5$ is —(NH(CO)—$CH_3$); and n is 1.

Embodiment 40 is the ligand of embodiment 36, wherein $R^1$ is H; X is —(OC)—O—B—O—Ar—(CO)—C(OH)$R^2_2$ wherein B is an alkylene group with 1-10 carbon atoms; Ar is a phenylene group; each $R^2$ is an alkyl group with 1-5 carbon atoms; and A is an alkylene group with 1-10 carbon atoms.

Embodiment 41 is the ligand of embodiment 36, wherein B is an ethylene group; each $R^2$ is a methyl group; and A is a propylene group.

Also included are embodiments of curable reaction mixtures. Embodiment 42 includes a curable reaction mixture comprising: at least one free radically polymerizable monomer; and surface-modified zirconia nanoparticles, wherein the surface-modified zirconia nanoparticles comprise: zirconia nanoparticles; and at least one ligand attached to at least one of the zirconia nanoparticles, the ligand comprising: a hydroxamate functionality; and a reactive group comprising a chain transfer group or a photoinitiator group.

Embodiment 43 is the curable reaction mixture of embodiment 42, wherein the chain transfer group comprises a thiol group.

Embodiment 44 is the curable reaction mixture of embodiment 42 or 43, wherein the ligand comprises the structure: $R^1N(OH)(CO)$-A-X wherein $R^1$ is selected from a hydrogen atom, an alkyl group, a cycloalkyl group, an aryl group, a heteroaryl group, an aralkyl group, a heteroaryl group, or a heterocycloalkyl group; (CO) is a carbonyl group C=O; A is a divalent linking group selected from alkylene, arylene, aralkylene, heteroalkylene, heteroarylene, or heteroaralkylene; and X is —SH or —(OC)—O—B—O—Ar—(CO)—C(OH)$R^2_2$ wherein B is an alkylene group or arylene group; Ar is an aryl or substituted aryl group; and each $R^2$ is an alkyl group.

Embodiment 45 is the curable reaction mixture of any of embodiments 42-44, wherein the surface-modified zirconia nanoparticles further comprising at least one additional ligand comprising a hydroxamate functionality.

Embodiment 46 is the curable reaction mixture of embodiment 45, wherein the at least one additional ligand comprises the structure: $R^1N(OH)(CO)$—$R^3$ wherein $R^1$ is selected from a hydrogen atom, an alkyl group, a cycloalkyl group, an aryl group, a heteroaryl group, an aralkyl group, a heteroaryl group, or a heterocycloalkyl group; (CO) is a carbonyl group C=O; and $R^3$ is an alkyl group, a cycloalkyl group, an aryl group, a heteroaryl group, an aralkyl group, a heteroaryl group, or a heterocycloalkyl group.

Embodiment 47 is the curable reaction mixture of embodiment 46, wherein $R^3$ is a polar or non-polar compatibilizing group.

Embodiment 48 is the surface-modified nanoparticles of embodiment 47, wherein the polar compatibilizing group, if present, is selected from a hydroxyl group, a carboxylic acid group, an amine group, a thiol, an epoxide, an aziridine, an azide, a halide, an alkyne, an olefin, or a combination thereof.

Embodiment 49 is the surface-modified nanoparticles of embodiment 47, wherein the non-polar compatibilizing group, if present, is selected from alkyl, alkylene, heteroalkyl, aryl, arylene, or combinations thereof.

Embodiment 50 is the surface-modified nanoparticles of any of embodiments 45-49, wherein the at least one additional ligand comprises up to 99% by moles of the total ligands.

Embodiment 51 is the surface-modified nanoparticles of any of embodiments 45-50, wherein the at least one additional ligand comprises up to 95% by moles of the total ligands.

Embodiment 52 is the surface-modified nanoparticles of any of embodiments 45-51, wherein the at least one additional ligand comprises up to 90% by moles of the total ligands.

Embodiment 53 is the surface-modified nanoparticles of any of embodiments 45-52, wherein the at least one additional ligand comprises up to 50% by moles of the total ligands.

Embodiment 54 is the surface-modified nanoparticles of any of embodiments 45-53, wherein the at least one additional ligand comprises up to 40% by moles of the total ligands.

Embodiment 55 is the surface-modified nanoparticles of any of embodiments 45-54, wherein the at least one additional ligand comprises up to 25% by moles of the total ligands.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. or Alfa Aesar; Ward Hill, Mass. unless otherwise noted. These abbreviations are used in the following examples: g=grams;

mL=milliliter; L=liter; mol=mole; mmol=millimole; MPa=MegaPascals; psig=pounds per square inch gauge; cm=centimeter.

| Table of Abbreviations | |
|---|---|
| Abbreviation | Description |
| AA | Acrylic Acid |
| DMF | Dimethyl formamide |
| Flex 10 | Bisaziridine crosslinker, synthesis provided below. |
| PE Film | Polyester film with a thickness of 2 mils (51 micrometers), commercially available from Mitsubishi Polyester Film, Greer, SC as "HOSTAPHAN 3SAB". |
| Photoinitiator | 1-[4-(2-Hydroxyethoxy)-phenyl]-2-hydroxy-2-methyl-1-propane-1-one, commercially available as "IRGACURE 2959" from Ciba Tarrytown, NY. |
| IOA | Isooctyl acrylate |
| IPA | Isopropyl Alcohol |
| Release Liner | Silicone coated polyethylene terephthalate, commercially available as "SILPHAN S36 M74 A" from Siliconature, Chicago, IL. |
| THF | Tetrahydrofuran |
| $ZrO_2$ Aqueous Sol | Synthesis provided below. |
| 2-BPHA | 6-(2-biphenoxy)hexyl acrylate, prepared as described in US Patent Publication No. 2009/0105437 (Determan et al.). |
| XL-353 | 2,4-bistrichloromethyl-6(4-methoxyphenyl)-s-triazine, an s-triazine photocrosslinker. |

Preparatory Examples

Synthesis of 1,10-decanediol bis(3-(2-methyl-aziridine-1-carbonyl)-benzoic acid)ester (Flex-10)

Flex 10, the bisaziridine crosslinker utilized in the examples, was prepared according to Preparative Example 1 of published US Pat. Appl. No. 2010-0227969 (Zhu, et al.).

Part A. Synthesis of 1,10-decanediol bis(3-chlorocarbonylbenzoic acid)ester

To a 3 L, three-neck, round bottom flask equipped with a magnetic stirrer, a thermometer, and a bubbler was added isophthaloyl dichloride (1950 g, 9.60 mol). The flask was heated at 55° C. To the flask was added 1,10-decanediol (112 g, 0.64 mol) in portions. After stirring the reaction mixture at 55° C. for 1 hour, the excess isophthaloyl dichloride was removed by vacuum distillation (200 mTorr, 100° C.) and was recycled. A stream of dry nitrogen was bubbled through the mixture while distilling so the isophthaloyl dichloride residue could be removed completely. A white solid (311 g) was obtained as product.

Part B. Synthesis of 1,10-decanediol bis(3-(2-methyl-aziridine-1-carbonyl)-benzoic acid)ester (Flex-10)

To a 3 L, three-neck, round bottom flask equipped with a magnetic stirrer, a thermometer, and an addition funnel were added an aqueous NaOH solution (563 g of a 10.0 weight percent solution), toluene (500 mL), and 2-methylaziridine (89.3 g of 90% pure 2-methylaziridine, 1.41 mol). The mixture was stirred and cooled to −10° C. to −5° C. To this stirred mixture was added 1,10-decanediol bis(3-chlorocarbonyl-benzoic acid) ester (311 g) in toluene (500 mL) solution over a period of 30 minutes. When addition was complete, the mixture was stirred at room temperature overnight. The organic phase was then washed with water, dried over magnesium sulfate ($MgSO_4$), filtered and concentrated under vacuum at room temperature to give 331.5 g of 1,10-decanediol bis(3-(2-methylaziridine-1-carbonyl)benzoic acid) ester (Flex-10) as a pale yellow oil Synthesis of $ZrO_2$ Aqueous Sol The $ZrO_2$ aqueous sol used in the below examples was prepared according to the procedure outlined in Example 6 of U.S. Pat. No. 7,429,422 (Davidson et al.). In a glass vessel, yttrium acetate hydrate (51.4 grams) was dissolved in Zirconium Acetate Solution (2,000 grams) and the solution was concentrated to 60 percent solids using a rotary evaporator. Zirconium Acetate Solution is an aqueous solution of zirconium acetate containing 14.8 wt % Zr that is available from Nyacol Nano Technologies, Inc., Ashland, Mass. The concentrate was diluted with sufficient DI water to give a 12.5 wt % solution (first feedstock).

The first feedstock was pumped at a rate of 80 mL/min through 100 feet (30 meters) of stainless-steel tubing that was immersed in a bath of oil heated to 206° C. The stainless-steel tubing had an outer diameter of 0.25 inch (0.64 cm) and a wall thickness of 0.035 inch (0.089 cm). Following the reactor tube, the material passed through a coil of an additional 20 feet (6 meters) of stainless-steel tubing that was immersed in an ice-water bath to cool the material. The stainless-steel tubing has an outer diameter of 0.25 inch (0.64 cm) and a wall thickness of 0.035 inch (0.089 cm). A backpressure regulator valve was used to maintain an exit pressure of 240 to 310 psig (1.76 to 2.24 MPa). The product was a liquid suspension of fine particles of a white solid. The percent conversion of the zirconium-containing intermediate was 52%.

The liquid suspension was concentrated to 15 wt % solids using a rotary evaporator. This concentrate was pumped at a rate of 15 mL/min through 100 feet (30 meters) of stainless-steel tubing that was immersed in a bath of oil heated to 206° C. The stainless-steel tubing had an outer diameter of 0.25 inch (0.64 cm) and a wall thickness of 0.035 inch (0.089 cm). Following the reactor tube, the material passed through a coil of an additional 20 feet (6 meters) of stainless-steel tubing that was immersed in an ice-water bath to cool the material. The stainless-steel tubing had an outer diameter of 0.25 inch (0.64 cm) and a wall thickness of 0.035 inch (0.089 cm). A backpressure regulator valve was used to maintain an exit pressure of 250 to 300 psig (1.83 to 2.17 MPa). The product was a zirconia aqueous sol ($ZrO_2$ sol).

General Procedure for the Preparation of Dimethyl Formamide Solutions of Nanozirconia The aqueous solution of acetate-stabilized nanozirconia (50.3836 g sol, 20.77 g $ZrO_2$) was added to a 250 mL round-bottomed flask. Dimethyl formamide (200 mL) was added, and the mixture concentrated in vacuo at 45-50° C. to approximately 50-65 g of solution four times. The mass of the final $ZrO_2$/DMF solution was 52.6504 g (39.45 mass % $ZrO_2$).

Preparatory Example PE-1

Synthesis of Hydroxamic Acid Ligand 2 via Reaction of (+/−)-Dodecanolactone with Hydroxylamine

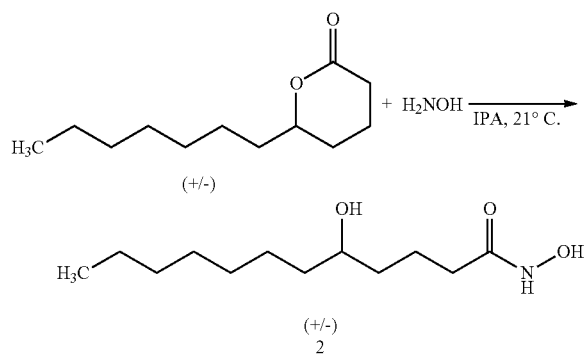

A 1-L round-bottomed flask equipped with a magnetic stir bar was charged with isopropanol (340 mL). (+/−)-Dodecanolactone (67.2 g, 339 mmol) was added with stirring and the mixture became homogeneous. A 50 wt % solution of hydroxylamine in water (20 mL, 22.4 g, 339 mmol) was added to the reaction mixture. The reaction vessel warmed slightly and was gently capped with a yellow plastic cap. After 3 days, the heterogeneous reaction mixture was concentrated to dryness in vacuo to a white solid. The solid was recrystallized from ethyl acetate (200 mL). The white solid was collected by vacuum filtration and washed with ethyl acetate (100 mL). Residual solvent was removed by high vacuum to provide 2 (37.83 g, 163.5 mmol, 48%) as white flakes. $^1$H NMR (400 MHz, DMSO) δ 10.30 (1H, s, NHOH), 8.64 (1H, s, NHOH), 4.26 (1H, d, J=5.3 Hz, CHOH), 1.91 (2H, t, J=7.4 Hz, CH$_2$C=O), 1.65-1.52 (1H, m, aliphatic CH), 1.52-1.40 (1H, m, aliphatic CH), 1.38-1.16 (14H, m, aliphatic CH), 0.86 (3H, app. t, J=6.6 Hz, CH$_2$CH$_3$); $^{13}$C NMR (101 MHz, DMSO) δ 169.2, 69.3, 37.2, 36.6, 32.4, 31.3, 29.2, 28.8, 25.3, 22.1, 21.6, 14.0; MS (ES) m/z for C$_{12}$H$_{24}$NO$_3$ [M−H]$^-$ calcd. 230.2. found 230.2.

Instrumentation.

Proton nuclear magnetic resonance ($^1$H NMR) spectra and carbon nuclear magnetic resonance ($^{13}$C NMR) spectra were recorded on a 400 MHz spectrometer. Chemical shifts for protons are reported in parts per million downfield from tetramethylsilane and are referenced to residual protium in the NMR solvent (CHCl$_3$: δ 7.26; (CD$_2$H)$_2$SO: δ 2.50; CD$_2$HOH: δ 3.51, CD$_2$H(CD$_3$)NC(O)D: δ 2.92). Chemical shifts for carbon are reported in parts per million downfield from tetramethylsilane and are referenced to the carbon resonances of the solvent (CDCl$_3$: δ 77.16; (CD$_3$)$_2$SO: δ 39.52; CD$_3$OD: δ 49.00, (CD$_3$)$_2$NC(O)D: δ 34.89). Data are presented as follows: chemical shift, integration, multiplicity (br=broad, s=singlet, d=doublet, t=triplet, q=quartet, quint.=quintuplet, m=multiplet), coupling constants in Hertz (Hz), and assignment.

Refractive indices of composite materials were measured on an Abbe Refractometer, commercially available from Milton Roy Co. (Ivyland, Pa.).

Test Methods

180° Peel Adhesion

This peel adhesion test is similar to the test method described in ASTM D 3330-90, substituting a glass substrate for the stainless steel substrate described in the test.

Adhesive coatings on polyester film were cut into 1.27 centimeter by 10 centimeter strips. Each strip was then adhered to a 10 centimeter by 20 centimeter clean, solvent washed glass coupon using a 2-kilogram roller passed once over the strip. The bonded assembly dwelled at room temperature for about 15 minutes and was tested for 180° peel adhesion using an IMASS slip/peel tester (Model 3M90, commercially available from Instrumentors Inc., Strongsville, Ohio) at a rate of 30 centimeters/minute (12 inches/minute) over a five second data collection time. Two samples were tested; the reported peel adhesion value is an average of the peel adhesion value from each of the two samples. Data was recorded in ounces/inch and converted to Newtons/decimeter N/dm.

Shear Strength

This shear strength test is similar to the test method described in ASTM D 3654-88.

Adhesive coatings on polyester film were cut into 1.27 centimeter (0.5 inch) by 15 centimeter (6 inch) strips. Each strip was then adhered to a stainless steel panel such that a 1.27 centimeter by 1.27 centimeter portion of each strip was in firm contact with the panel and one end portion of the tape being free. The panel with coated strip attached was held in a rack such that the panel formed an angle of 178° with the extended tape free end which was tensioned by application of a force of one kilogram applied as a hanging weight from the free end of the coated strip. The 2° less than 180° was used to negate any peel forces, thus ensuring that only shear strength forces were measured, in an attempt to more accurately determine the holding power of the tape being tested. The time elapsed for each tape example to separate from the test panel was recorded as the shear strength. All shear strength failures (if the adhesive failed at less than 10,000 minutes) reported herein were cohesive failures of the adhesive. Each test was terminated at 10,000 minutes, unless the adhesive failed at an earlier time (as noted).

Example 1

Synthesis of Thiol-Functionalized Hydroxamic Acid Ligand 1

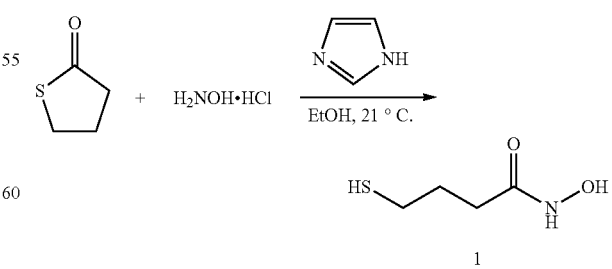

A 100 mL round-bottomed flask equipped with a magnetic stir bar was charged with hydroxylamine hydrochloride (1.61 g, 23.1 mmol) and imidazole (1.56 g, 22.9 mmol). Ethanol (40 mL) was added with stirring, and the flask was sealed with a rubber septum. Nitrogen was bubbled through the heterogeneous solution for 25 minutes. Then, γ-thiobutyrolactone (2.0 mL, 23.1 mmol) was added over 5-10 seconds. The reaction mixture became clear, colorless, and homogeneous within 2 hours. After 2.75 hours, the reaction mixture was concentrated in vacuo to a clear and colorless liquid. $^1$H NMR analysis indicated clean conversion to the desired product. The liquid was left under vacuum for 18 h. The oil was then dissolved in hydrochloric acid (1N, 20 mL) and transferred to a 125 mL separatory funnel. The aqueous solution was washed with chloroform (1×40 mL) and ethyl acetate (4×40 mL). The organic washes were combined and nitrogen was bubbled through the organic solution as it was collected. The combined organic solution was dried over sodium sulfate as nitrogen was bubbled through the solution. The solution was filtered and concentrated in vacuo to provide 1 (1.31 g, 9.69 mmol, 42%) as a white solid. $^1$H NMR (400 MHz, DMSO) δ 10.39 (1H, s, NHOH), 8.70 (1H, s, NHOH), 2.45 (2H, dt, J=7.2, 7.2 Hz, CH$_2$SH), 2.32 (1H, t, J=7.9 Hz, SH), 2.05 (2H, t, J=7.3 Hz, CH$_2$C=O), 1.74 (2H, app. quint., J=7.2 Hz, CH$_2$CH$_2$C=O); $^{13}$C NMR (101 MHz, DMSO) δ 168.6, 30.9, 29.5, 23.5; MS (ES) m/z for C$_4$H$_8$NO$_2$S [M−H]$^-$ calcd. 134.0. found 134.0.

Example 2

Synthesis of Thiol-Functionalized Hydroxamic Acid Ligand 3

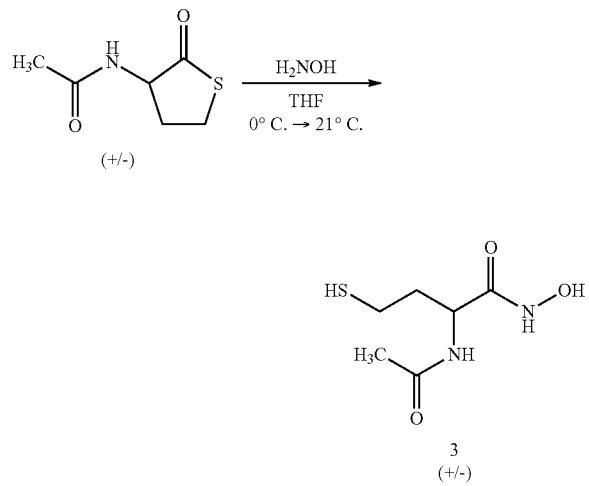

A 250 mL round-bottomed flask equipped with a magnetic stir bar and a rubber septum was charged with tetrahydrofuran (110 mL) and sparged with nitrogen for 20 minutes. The reaction was kept under nitrogen. A 50 wt. % solution of hydroxylamine in water (1.85 mL, 1.04 g, 31.4 mmol) was added. Then, (±)N-acetylhomocysteinethiolactone (5.00 g, 31.4 mmol) was added in small portions over approximately 10 minutes. The reaction was sparged with nitrogen for 1 minute and then stirred under a nitrogen atmosphere. After 1 hour, the reaction was sampled and the sample was concentrated in vacuo to a white solid. $^1$H NMR (500 MHz, DMSO) analysis was consistent with formation of the desired thiol-functionalized hydroxamic acid 3. $^1$H NMR (400 MHz, DMSO) δ 10.58 (1H, s, NHOH), 8.80 (1H, s, NHOH), 8.02 (1H, d, J=8.2 Hz, CH$_3$C(O)NH), 4.26 (1H, ddd, J=8.3, 8.3, 6.0 Hz, O=CCHNH), 2.46-2.34 (3H, m, CH$_2$SH), 1.86-1.78 (2H, m, CH$_2$CH$_2$SH), 1.83 (3H, s, CH$_3$C(O)NH); $^{13}$C NMR (101 MHz, DMSO) δ 169.1, 167.8, 49.2, 36.5, 22.4, 20.3. $^1$H NMR (400 MHz, DMF) δ 10.02 (1H, s, NHOH), 9.05 (1H, s, NHOH), 7.99 (1H, d, J=7.9 Hz, CH$_3$C(O)NH), 4.45 (1H, ddd, J=8.3, 8.3, 5.7 Hz, O=CCHNH), 2.61-2.49 (2H, m, CH$_2$SH), 2.28-2.10 (1H, m, CH$_2$SH), 2.02-1.87 (2H, m, CH$_2$CH$_2$SH), 1.93 (3H, s, CH$_3$C(O)NH); $^{13}$C NMR (101 MHz, DMF) δ, 169.9, 168.6, 50.2, 37.3, 22.4, 20.9. MS (ES) m/z for C$_6$H$_{11}$N$_2$O$_3$S [M−H]$^-$ calcd. 191.0. found 191.0; m/z for C$_6$H$_{13}$N$_2$O$_3$S [M+H]$^+$ calcd. 193.1. found 193.0. The mass of the final solution was approximately 94.4 g.

Example 3

Synthesis of Photoinitiator-Functionalized Hydroxamic Acid Ligand 4

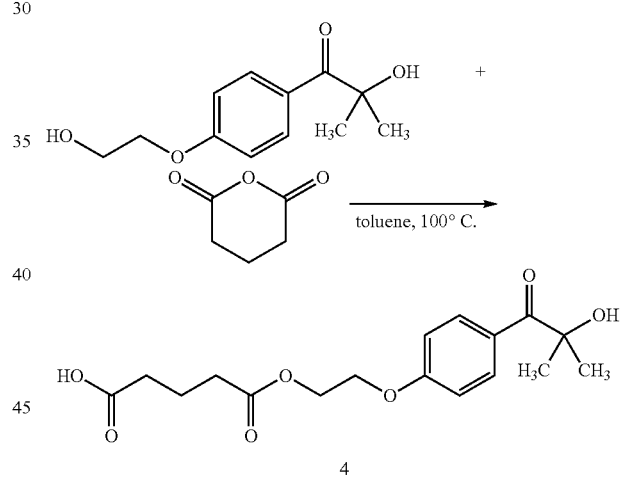

An approximately 100 mL glass vial equipped with a magnetic stir bar was charged with Photoinitiator (10.0 g, 44.6 mmol) and glutaric anhydride (5.09 g, 44.6 mmol). Toluene (40 mL) was added and the vial was sealed with a TEFLON-lined metal cap and then further sealed with TEFLON tape and electrical tape. With stirring, the mixture was heated to 110° C. in an oil bath. After 18 hours, the homogeneous reaction mixture was removed from the oil bath and allowed to cool to room temperature. The reaction mixture was concentrated in vacuo to provide crude 4 as a very pale yellow, viscous oil. The reaction had proceeded to approximately 90% conversion by $^1$H-NMR analysis. $^1$H NMR (400 MHz, CDCl$_3$) δ 8.06 (2H, d, J=8.9 Hz, ArH), 6.95 (2H, d, J=8.9 Hz, ArH), 4.46 (2H, t, J=4.6 Hz, ArOCH$_2$), 4.25 (2H, t, J=4.6 Hz, CH$_2$CH$_2$OAr), 2.48-2.40 (4H, m, O=CCH$_2$CH$_2$CH$_2$C=O), 1.96 (2H, app. quint., J=7.3 Hz, O=CCH$_2$CH$_2$CH$_2$C=O), 1.63 (6H, s, CH$_3$).

Example 4

Synthesis of Photoinitiator-Functionalized Hydroxamic Acid Ligand 5

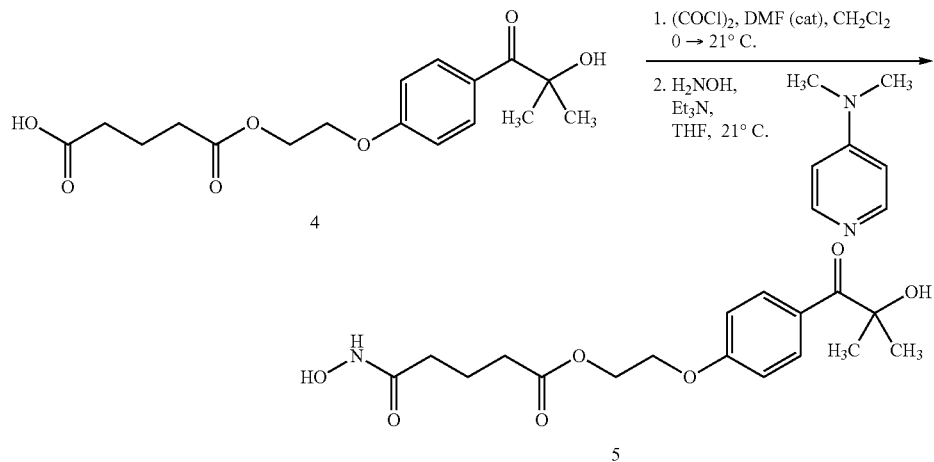

A 250 mL round-bottomed flask equipped with a magnetic stir bar was charged with 4 (5.17 g, 15.3 mmol) and dichloromethane (50 mL). The flask was sealed with a rubber septum and a nitrogen inlet line was added. The headspace was purged with nitrogen for 5 minutes. Dimethylformamide (0.040 mL) was added and the reaction mixture was cooled to 0° C. with stirring. Oxalyl chloride (1.60 mL, 18.9 mmol) was added dropwise over 3 minutes. The reaction was stirred at 0° C. for 30 minutes and was then allowed to warm to 20° C. After an additional 1 hour, gas evolution had ceased. The reaction was concentrated in vacuo to a pale yellow viscous oil.

The acid chloride intermediate (1.00 g, 2.80 mmol) was added to a 20 mL glass vial. Tetrahydrofuran (5.0 mL) and 4-(dimethylamino)pyridine (0.017 g, 0.14 mmol) were added and the solution was mixed until homogeneous. Triethylamine (0.30 mL, 0.218 g, 2.15 mmol) was added and a white precipitate formed immediately. A 50 wt. % solution of hydroxylamine in water (0.165 mL, 0.0926 g, 2.80 mmol) was added followed by an additional portion of triethylamine (0.290 mL, 0.211 g, 2.08 mmol). The reaction was sealed with a plastic cap and stirred at room temperature. After 15 minutes, the reaction was transferred to a 125 mL reparatory funnel using ethyl acetate (40 mL) and aqueous hydrochloric acid (1N, 40 mL). The solution was mixed well and separated. The aqueous layer was back extracted with ethyl acetate (2×40 mL). The combined organic solution was dried over sodium sulfate for 10 minutes, then filtered and concentrated in vacuo to a pale yellow viscous oil. The crude product was purified via flash chromatography on silica gel (98:02 to 97:03 ethyl acetate:methanol gradient) to provide the product 5 as a very pale yellow viscous oil (0.576 g, 1.63 mmol, 58%). $^1$H NMR (400 MHz, DMSO) δ 10.37 (1H, s, NHOH), 8.69 (1H, s, NHOH), 8.20 (2H, d, J=8.9 Hz, ArH), 7.02 (2H, d, J=8.9 Hz, ArH), 4.39-4.33 (2H, m, ArOCH$_2$), 4.30-4.23 (2H, m, ArOCH$_2$CH$_2$O), 2.36-2.26 (2H, m, O=CCH$_2$CH$_2$CH$_2$C=O), 2.03-1.94 (2H, m, O=CCH$_2$CH$_2$CH$_2$C=O), 1.74 (2H, app. quint., J=7.3 Hz, O=CCH$_2$CH$_2$CH$_2$C=O), 1.38 (6H, s, CH$_3$); $^{13}$C NMR (101 MHz, DMSO) δ 202.9, 173.0, 170.3, 162.3 132.6, 126.8, 114.4, 76.2, 66.2, 62.7, 33.0, 31.7, 28.8, 25.5.

Example 5

Preparation of Zirconia Particles Functionalized with Ligands 1 and 2

Example 5A 50 mol % Ligand 1, 50 mol % Ligand 2

The ZrO$_2$/dimethyl formamide solution prepared as above (0.500 g sol, 0.197 g ZrO$_2$) was added to a 20 mL glass vial. Ligand 1 (0.0190 g, 0.138 mmol) was added and the solution was mixed well. The homogeneous solution was allowed to stand for 20 minutes. Then, ligand 2 (0.0319 g, 0.138 mmol) was added, and the mixture was mixed well. Most of the ligand dissolved. Isooctyl acrylate (1.20 mL, 1.06 g, 5.73 mmol) was added to provide a milky white mixture. Tetrahydrofuran (11 mL) was added and the mixture was sonicated for 20 minutes to provide a clear, homogeneous dispersion. The final mixture was 1.74 mass % ZrO$_2$ and 9.32 mass % isooctyl acrylate.

Examples 5B-5K

A series of ZrO$_2$/dimethyl formamide solutions were prepared and functionalized with various ratios of Ligand 1 and Ligand 2, using the procedures described above for the Example 5A. The ratio of ligands used is shown in Table 1 below.

TABLE 1

| Example | Mol % Ligand 1 | Mol % Ligand 2 |
|---|---|---|
| 5A | 50 | 50 |
| 5B | 50 | 50 |
| 5C | 50 | 50 |
| 5D | 33 | 67 |
| 5E | 25 | 75 |
| 5F | 75 | 25 |
| 5G | 75 | 25 |
| 5H | 100 | 0 |
| 5I | 100 | 0 |
| 5J | 75 | 25 |
| 5K | 75 | 25 |

Preparation of Zirconia Particles Functionalized with Polymeric Ligands

Example 6

Preparation of Zirconia Particles with Isooctyl Acrylate Functional Ligands

Example 6A

The solution of functionalized $ZrO_2$ in dimethyl formamide as prepared above in Example 5B (2.03 g, 0.0353 g $ZrO_2$, 0.189 g isooctyl acrylate) was added to a 20 mL glass vial. An additional portion of isooctyl acrylate (0.300 mL, 0.264 g, 1.43 mmol) was added to bring the total isooctyl acrylate content to 0.453 g, (2.46 mmol). Photoinitiator (0.0015 g, 0.007 mmol) was added. The mixture was sparged for 7 minutes and then sealed with a TEFLON-lined plastic cap, TEFLON tape, and electrical tape. The reaction was irradiated (λ=350 nm) with stirring. After approximately 21 hours, the reaction was opened to air. $^1$H NMR analysis indicated the presence of acrylate polymer (~94% conversion). The solution was concentrated in vacuo to a very viscous, clear, colorless liquid. The material was 6.93 mass % $ZrO_2$, as determined by TGA, and had a refractive index of 1.4765.

Examples 6B-6K

The series of isooctyl acrylate functionalized $ZrO_2$/particle prepared and functionalized with various ratios of Ligand 1 and Ligand 2, using the procedures described above for Example 6A, using the solutions prepared in the Examples 5C-5K. The mass % $ZrO_2$, as determined by TGA, and refractive index were measured on an Abbe Refractometer and are shown in Table 2 below.

TABLE 2

| Example | Example Solution | mass % $ZrO_2$ | Refractive Index (n) |
|---|---|---|---|
| 6A | 5B | 6.93 | 1.4765 |
| 6B | 5A | 21.03 | 1.4992 |
| 6C | 5C | 28.87 | 1.5140 |
| 6D | 5D | 38.26 | 1.5363 |
| 6E | 5E | 36.70 | 1.5330 |
| 6F | 5F | 37.08 | 1.5352 |
| 6G | 5G | 57.70 | 1.6042 |
| 6H | 5H | 58.64 | 1.6056 |
| 6I | 5I | 50.94 | 1.5754 |
| 6J | 5J | 52.61 | 1.5814 |
| 6K | 5K | 63.56 | 1.6380 |

Example 7

Polymer-Functionalized Zirconia Nanoparticles Prepared from Isooctyl Acrylate and 2-Phenoxyethyl Acrylate or 6-(2-biphenoxy)hexyl acrylate

Example 7A

Step 1: Zirconia Particles Functionalized with 75 mol % Ligand 1 and 25 mol % Ligand 2

The $ZrO_2$/dimethyl formamide solution prepared as above (1.00 g sol, 0.395 g $ZrO_2$) was added to a 20 mL glass vial. Ligand 1 (0.0560 g, 0.414 mmol) was added and the solution was mixed well. The homogeneous solution was allowed to stand for 35 minutes under nitrogen. Then, ligand 2 (0.0319 g, 0.138 mmol) and tetrahydrofuran (1.5 mL) were added. Isooctyl acrylate (0.090 mL, 0.0792 g, 0.430 mmol) was added to provide a heterogeneous mixture. The mixture was sonicated for 10 minutes to provide a slightly hazy, but well-dispersed solution. The mass of the final solution was 2.4209 g (16.3 mass % $ZrO_2$, 3.27 mass % isooctyl acrylate).

Step 2: Zirconia Particles Functionalized with Isooctyl Acrylate and 2-Phenoxyethyl Acrylate The solution of functionalized $ZrO_2$ in dimethyl formamide as prepared in Step 1 above (1.179 g, 0.192 g $ZrO_2$, 0.0385 g isooctyl acrylate) was added to a 20 mL glass vial. 2-Phenoxyethyl acrylate (0.157 g, 0.817 mmol) and a magnetic stir bar were added. Photoinitiator (0.0015 g, 0.007 mmol) was added. The mixture was sparged with nitrogen for 5 minutes and was then sealed with a TEFLON-lined plastic cap, TEFLON tape, and electrical tape. The reaction was irradiated (λ=350 nm) with stirring. After approximately 16.5 hours, the reaction was opened to air. $^1$H NMR analysis indicated the presence of acrylate polymer (~100% conversion). The solution was concentrated in vacuo (~24 hours, 60° C., ~0.010 mmHg) to a sticky, clear, colorless, waxy solid. The material was 44.60 mass % $ZrO_2$, as determined by TGA, and had a refractive index of 1.6205.

Example 7B

Step 1: Zirconia Particles Functionalized with 75 mol % Ligand 1 and 25 mol % Ligand 2

The same procedure as was used in Example 7A, Step 1 was followed.

Step 2: Zirconia Particles Functionalized with Isooctyl Acrylate and 6-(2-biphenoxy)hexyl acrylate The solution of functionalized $ZrO_2$ in dimethyl formamide as prepared in Step 1 above (1.179 g, 0.192 g $ZrO_2$, 0.0385 g isooctyl acrylate) was added to a 20 mL glass vial. 6-(2-biphenoxy)hexyl acrylate (0.157 g, 0.817 mmol) and a magnetic stir bar were added. Photoinitiator (0.0015 g, 0.007 mmol) was added. The mixture was sparged with nitrogen for 5 minutes and was then sealed with a TEFLON-lined plastic cap, TEFLON tape, and electrical tape. The reaction was irradiated (λ=350 nm) with stirring. After approximately 16.5 hours, the reaction was opened to air. The solution was concentrated in vacuo (~4 days, 65° C., ~0.010 mmHg) to a sticky, clear, very pale yellow, waxy solid. The material was 48.41 mass % $ZrO_2$, as determined by TGA, and had a refractive index of 1.6420.

Example 8

Preparation of Zirconia Particles with Polymer Functional Ligands Via a One Pot Synthesis

Example 8A

Zirconia Particles Functionalized with Isooctyl Acrylate and 6-(2-biphenoxy)hexyl acrylate Step 1: One-Pot Preparation of Thiol-Functionalized Zirconia Nanoparticles with Ligand 1.

A 100 mL round-bottomed flask equipped with a magnetic stir bar and a rubber septum was charged with tetrahydrofuran (30 mL) and sparged with nitrogen for 20 minutes. The reaction was kept under nitrogen. A 50 wt. % solution of hydroxylamine in water (0.510 mL, 0.286 g, 8.65 mmol) was added. Then, γ-thiobutyrolactone (0.750 mL, 0.885 g, 8.66 mmol) was added over 5-10 seconds. The reaction was sparged with nitrogen for 1 minute and then stirred under a nitrogen atmosphere. After 3.75 hours, the reaction was sampled and the sample was concentrated in vacuo to a colorless oil. $^1$H NMR (500 MHz, DMSO) analysis was consistent with formation of the desired thiol-functionalized hydroxamic acid 1 (~90% desired product). An aqueous solution of acetate-stabilized zirconia (20.00 g sol, 8.2458 g $ZrO_2$) was added to the reaction solution. The homogeneous mixture was stirred for 20 minutes. Then, ligand 2 (0.668 g, 2.89 mmol) was added and the reaction was mixed well to provide a somewhat cloudy, but well-dispersed solution. The mass of the final solution was 43.44 g (~19.0 mass % $ZrO_2$).

Step 2: Zirconia Particles Functionalized with Isooctyl Acrylate and 6-(2-biphenoxy)hexyl acrylate (2-BPHA: IOA=0.80:0.20 wt. fraction)

Approximately 95% (41.44 g) of the solution of functionalized zirconia nanoparticles from Step 1 above was concentrated to dryness in vacuo to provide a white solid. 6-(2-biphenoxy)hexylacrylate (6.31 g, 19.5 mmol) and isooctyl acrylate (1.62 g, 8.79 mmol) were added. Tetrahydrofuran was added to bring the total mass of the solution to 52.40 g (15 mass % $ZrO_2$). The mixture was sonicated for 30 minutes to provide a well-dispersed, but slightly hazy solution. The solution was transferred to an approximately 100 mL glass bottle. Photoinitiator (0.063 g, 0.28 mmol) was added. The solution was sparged with nitrogen for 15 minutes and then sealed with a TEFLON-lined metal cap, TEFLON tape, and electrical tape. The reaction was placed in front of a lamp ($\lambda$=350 nm) and irradiated with stirring. After 24 hours, the reaction was opened to air and sampled. $^1$H NMR analysis was consistent with the production of acrylate polymer (>90% conversion). The reaction was concentrated in vacuo (50-75° C., ~0.01 mmHg) for 5 days to remove residual solvent. The final material contained 46.5% $ZrO_2$ as determined by TGA. The refractive index of the clear and colorless material was 1.6290.

Example 8B

Zirconia Particles Functionalized with Isooctyl Acrylate and 6-(2-biphenoxy)hexyl acrylate Step 1: One-Pot Preparation of Thiol-Functionalized Zirconia Nanoparticles with Ligand 1.

The same procedure as was used in Example 8A, Step 1 was followed.

Step 2: Zirconia Particles Functionalized with Isooctyl Acrylate and 6-(2-biphenoxy)hexyl acrylate (2-BPHA: IOA=0.80:0.20 wt. fraction)

Approximately 5% (2.0 g) of the solution of functionalized zirconia nanoparticles from Step 1 above was concentrated to dryness in vacuo to provide a white solid. 6-(2-biphenoxy)hexylacrylate (0.310 g, 0.96 mmol) and isooctyl acrylate (0.076 g, 0.41 mmol) were added. Tetrahydrofuran was added to bring the total mass of the solution to 2.40 g (15 mass % $ZrO_2$). The mixture was sonicated for 10 minutes to provide a well dispersed, but slightly hazy solution. The solution was transferred to an approximately 20 mL glass bottle. Photoinitiator (0.0032 g, 0.014 mmol) was added. The solution was sparged with nitrogen for 6 minutes and then sealed with a TEFLON-lined metal cap, TEFLON tape, and electrical tape. The reaction was placed in front of a lamp ($\lambda$=350 nm) and irradiated with stirring. After 20 hours, the reaction was opened to air and sampled. $^1$H NMR analysis was consistent with the production of acrylate polymer (>90% conversion). The reaction was concentrated in vacuo (50° C., ~0.01 mmHg) for 2 days to remove residual solvent. Based on the mass of zirconia, ligands, and monomers used, the final material contained approximately 46 wt. % zirconia. The refractive index of the clear and colorless material was 1.6245.

Example 8C

Zirconia Particles Functionalized with Isooctyl Acrylate and 6-(2-biphenoxy)hexyl acrylate Step 1: One-Pot Preparation of Thiol-Functionalized Zirconia Nanoparticles with Ligand 1.

A 500 mL round-bottomed flask equipped with a magnetic stir bar and a rubber septum was charged with tetrahydrofuran (120 mL) and sparged with nitrogen for 35 minutes. The reaction was kept under nitrogen. A 50 wt. % solution of hydroxylamine in water (2.00 mL, 1.12 g, 33.9 mmol) was added. Then, γ-thiobutyrolactone (3.00 mL, 34.7 mmol) was added over 5-10 seconds. The reaction was sparged with nitrogen for 1 minute and then stirred under a nitrogen atmosphere. After 3.75 hours, the reaction was sampled and the sample was concentrated in vacuo to a colorless oil. $^1$H NMR (500 MHz, DMSO) analysis was consistent with formation of the desired thiol-functionalized hydroxamic acid 1 (~90% desired product). An aqueous solution of acetate-stabilized zirconia (80.0 g sol, 32.98 g $ZrO_2$) was added to the reaction. The homogeneous solution was allowed to stand for 15 minutes. Then, ligand 2 (2.67 g, 11.5 mmol) was added and the reaction was mixed well to provide a somewhat cloudy, but well-dispersed solution.

Step 2: Zirconia Particles Functionalized with Isooctyl Acrylate and 6-(2-biphenoxy)hexyl acrylate (2-BPHA: IOA=0.80:0.20 wt. fraction)

One half of the solution of functionalized zirconia nanoparticles from Step 1 above was concentrated to dryness in vacuo to provide a white solid. 6-(2-biphenoxy)hexylacrylate (11.32 g, 34.9 mmol) and isooctyl acrylate (2.83 g, 15.4 mmol) were added. Tetrahydrofuran was added to bring the total mass of the solution to 109.9 g (15 mass % $ZrO_2$). The mixture was sonicated for 25 minutes to provide a well-dispersed, but slightly hazy solution. The solution was transferred to an approximately 250 mL glass bottle. Photoinitiator (0.136 g, 0.61 mmol) was added. The solution was sparged with nitrogen for 20 minutes and then sealed with a TEFLON-lined metal cap, TEFLON tape, and electrical tape. The reaction was placed in front of a lamp ($\lambda$=350 nm) and irradiated with stirring. After 20 hours, the reaction was opened to air and sampled. $^1$H NMR analysis was consistent with the production of acrylate polymer (>90% conversion). The hazy blue reaction solution was concentrated in vacuo to a clear, but somewhat hazy, very viscous wax-like material. A small sample of the dry material was spread into a thin film onto a glass slide. The nanozirconia-filled material provided a clear, mostly colorless thin film. Based on the mass of zirconia, ligands, and monomers used, the final material contained approximately 48 wt. % zirconia.

Example 8D

Zirconia Particles Functionalized with Isooctyl Acrylate and 6-(2-biphenoxy)hexyl acrylate Step 1: One-Pot Preparation of Thiol-Functionalized Zirconia Nanoparticles with Ligand 1.

The same procedure as was used in Example 8C, Step 1 was followed.

Step 2: Zirconia Particles Functionalized with Isooctyl Acrylate and 6-(2-biphenoxy)hexyl acrylate (2-BPHA:IOA=0.80:0.20 wt. fraction)

One quarter of the solution of functionalized zirconia nanoparticles from Step 1 above was concentrated to dryness in vacuo to provide a white solid. 6-(2-biphenoxy)hexylacrylate (3.52 g, 10.9 mmol) and isooctyl acrylate (0.881 g, 4.78 mmol) were added. Tetrahydrofuran was added to bring the total mass of the solution to 54.97 g (15 mass % $ZrO_2$). The mixture was sonicated for 30 minutes to provide a well-dispersed, but slightly hazy solution. The solution was transferred to an approximately 250 mL glass bottle. Photoinitiator (0.066 g, 0.29 mmol) was added. The solution was sparged with nitrogen for 20 minutes and then sealed with a TEFLON-lined metal cap, TEFLON tape, and electrical tape. The reaction was placed in front of a lamp ($\lambda$=350 nm) and irradiated with stirring. After 68 hours, the reaction was opened to air and sampled. $^1$H NMR analysis was consistent with the production of acrylate polymer (>90% conversion). The hazy blue reaction solution was concentrated in vacuo to a clear, but somewhat hazy, very viscous foam-like material. A small sample of the dry material was spread into a thin film onto a glass slide. The nanozirconia-filled material provided a clear, mostly colorless thin film. Based on the mass of zirconia, ligands, and monomers used, the final material contained approximately 57 wt. % zirconia. The refractive index of the clear and colorless material was 1.6653.

Example 8E

Zirconia Particles Functionalized with Isooctyl Acrylate, Acrylic Acid and 6-(2-biphenoxy)hexyl acrylate Step 1: One-Pot Preparation of Thiol-Functionalized Zirconia Nanoparticles with Ligand 1.

The same procedure as was used in Example 8C, Step 1 was followed.

Step 2: Zirconia Particles Functionalized with Isooctyl Acrylate and 6-(2-biphenoxy)hexyl acrylate (2-BPHA:IOA:AA=0.78:0.20:0.02 wt. fraction)

One quarter of the solution of functionalized zirconia nanoparticles from Step 1 above was concentrated to dryness in vacuo to provide a white solid. 6-(2-biphenoxy)hexylacrylate (2.58 g, 7.94 mmol), isooctyl acrylate (0.644 g, 3.50 mmol), and acrylic acid (0.065 g, 0.90 mmol) were added. Tetrahydrofuran was added to bring the total mass of the solution to 54.97 g (15 mass % $ZrO_2$). The mixture was sonicated for 30 minutes to provide a well-dispersed, but slightly hazy solution. The solution was transferred to an approximately 250 mL glass bottle. Photoinitiator (0.066 g, 0.29 mmol) was added. The solution was sparged with nitrogen for 20 minutes and then sealed with a TEFLON-lined metal cap, TEFLON tape, and electrical tape. The reaction was placed in front of a lamp ($\lambda$=350 nm) and irradiated with stirring. After 44 hours, the reaction was opened to air and sampled. $^1$H NMR analysis was consistent with the production of acrylate polymer (>90% conversion). The hazy blue reaction solution was concentrated in vacuo to a clear, but somewhat hazy, very viscous foam-like material. A small sample of the dry material was spread into a thin film onto a glass slide. The nanozirconia-filled material provided a clear, mostly colorless thin film. Based on the mass of zirconia, ligands, and monomers used, the final material contained approximately 61 wt. % zirconia.

Example 8F

Zirconia Particles Functionalized with Isooctyl Acrylate and 6-(2-biphenoxy)hexyl acrylate (2-BPHA:IOA=0.80:0.20 wt. fraction)

Based on the general procedure detailed in Example 8C above, acrylate-functionalized nanozirconia was prepared from ligand 1 (1.44 mmol ligand 1), an aqueous solution of acetate-stabilized zirconia (25.09 g sol, 10.30 g $ZrO_2$), ligand 2 (3.00 g, 13.0 mmol), 6-(2-biphenoxy)hexylacrylate (7.92 g, 24.4 mmol), isooctyl acrylate (2.03 g, 11.0 mmol), and Photoinitiator (0.079 g, 0.35 mmol). The reaction mixture was diluted to 15 wt. % $ZrO_2$ using THF. The final acrylate-functionalized particles were obtained as an opaque sticky white solid. A small sample of the dry material was spread into a thin film on a glass slide. The nanozirconia-filled material provided a somewhat transparent and colorless thin film. Based on the mass of zirconia, ligands, and monomers used, the final material contained approximately 44 wt. % zirconia.

Example 8G

Zirconia Particles Functionalized with Isooctyl Acrylate, Acrylic Acid, and 6-(2-biphenoxy)hexyl acrylate (2-BPHA:IOA:AA=0.80:0.15:0.05 wt. fraction)

Based on the general procedure detailed in Example 8C above, acrylate-functionalized nanozirconia was prepared from ligand 1 (7.21 mmol ligand 1), an aqueous solution of acetate-stabilized zirconia (25.09 g sol, 10.30 g $ZrO_2$), ligand 2 (1.67 g, 7.21 mmol), 6-(2-biphenoxy)hexylacrylate (7.95 g, 24.5 mmol), isooctyl acrylate (1.49 g, 8.09 mmol), acrylic acid (0.490 g, 6.80 mmol), and Photoinitiator (0.079 g, 0.35 mmol). The reaction mixture was diluted to 15 wt. % $ZrO_2$ using THF. The final acrylate-functionalized particles were obtained as a clear, but somewhat hazy, very viscous waxy oil. A small sample of the dry material was spread into a thin film on a glass slide. The nanozirconia-filled material provided a very nice transparent and colorless thin film. Based on the mass of zirconia, ligands, and monomers used, the final material contained approximately 45 wt. % zirconia.

Example 8H

Zirconia Particles Functionalized with Isooctyl Acrylate, Acrylic Acid, and 6-(2-biphenoxy)hexyl acrylate (2-BPHA:IOA:AA=0.80:0.18:0.02 wt. fraction)

Based on the general procedure detailed in Example 8C above, acrylate-functionalized nanozirconia was prepared from ligand 1 (34.0 mmol ligand 1), an aqueous solution of acetate-stabilized zirconia (78.90 g sol, 32.38 g $ZrO_2$), ligand 2 (2.62 g, 11.3 mmol), 6-(2-biphenoxy)hexylacrylate (25.89 g, 79.8 mmol), isooctyl acrylate (5.82 g, 31.6 mmol), acrylic acid (0.647 g, 8.98 mmol), and Photoinitiator (0.259 g, 1.15 mmol). The reaction mixture was diluted to 15 wt. % $ZrO_2$ using THF. The final acrylate-functionalized particles were obtained as a clear, but somewhat hazy, faint yellow, very viscous waxy oil. A small sample of the dry material was spread into a thin film on a glass slide. The nanozirconia-filled material provided a transparent and almost colorless thin film. Based on the mass of zirconia, ligands, and monomers used, the final material contained approximately 45 wt. % zirconia.

Example 8I

Zirconia Particles Functionalized with Isooctyl Acrylate, Acrylic Acid, and 6-(2-biphenoxy)hexyl acrylate (2-BPHA:IOA:AA=0.80:0.18:0.02 wt. fraction)

Based on the general procedure detailed in Example 8C above, acrylate-functionalized nanozirconia was prepared from ligand 1 (34.0 mmol ligand 1), an aqueous solution of acetate-stabilized zirconia (78.90 g sol, 32.38 g $ZrO_2$), ligand 2 (2.62 g, 11.3 mmol), 6-(2-biphenoxy)hexylacrylate (20.13 g, 62.1 mmol), isooctyl acrylate (4.53 g, 24.58 mmol), acrylic acid (0.503 g, 6.98 mmol), and Photoinitiator (0.259 g, 1.15 mmol). The reaction mixture was diluted to 15 wt. % $ZrO_2$ using THF. The final acrylate-functionalized particles were obtained as a clear, but somewhat hazy, faint yellow, very viscous waxy oil. A small sample of the dry material was spread into a thin film on a glass slide. The nanozirconia-filled material provided a transparent and almost colorless thin film. Based on the mass of zirconia, ligands, and monomers used, the final material contained approximately 50 wt. % zirconia.

Example 8J

Zirconia Particles Functionalized with Isooctyl Acrylate, Acrylic Acid, and 6-(2-biphenoxy)hexyl acrylate (2-BPHA:IOA:AA=0.80:0.18:0.02 wt. fraction)

Based on the general procedure detailed in Example 8C above, acrylate-functionalized nanozirconia was prepared from ligand 1 (34.0 mmol ligand 1), an aqueous solution of acetate-stabilized zirconia (78.90 g sol, 32.38 g $ZrO_2$), ligand 2 (2.62 g, 11.3 mmol), 6-(2-biphenoxy)hexylacrylate (15.42 g, 47.5 mmol), isooctyl acrylate (3.47 g, 18.8 mmol), acrylic acid (0.385 g, 5.34 mmol), and Photoinitiator (0.259 g, 1.15 mmol). The reaction mixture was diluted to 15 wt. % $ZrO_2$ using THF. The final acrylate-functionalized particles were obtained as a clear, but somewhat hazy, very viscous waxy oil. A small sample of the dry material was spread into a thin film on a glass slide. The nanozirconia-filled material provided a very nice transparent and colorless thin film. Based on the mass of zirconia, ligands, and monomers used, the final material contained approximately 55 wt. % zirconia.

Example 8K

Zirconia Particles Functionalized with Isooctyl Acrylate, Acrylic Acid, and 6-(2-biphenoxy)hexyl acrylate (2-BPHA:IOA:AA=0.80:0.18:0.02 wt. fraction)

Based on the general procedure detailed in Example 8C above, acrylate-functionalized nanozirconia was prepared from ligand 1 (34.0 mmol ligand 1), an aqueous solution of acetate-stabilized zirconia (78.90 g sol, 32.38 g $ZrO_2$), ligand 2 (2.62 g, 11.3 mmol), 6-(2-biphenoxy)hexylacrylate (11.49 g, 35.42 mmol), isooctyl acrylate (2.59 g, 14.05 mmol), acrylic acid (0.287 g, 3.98 mmol), and Photoinitiator (0.259 g, 1.15 mmol). The reaction mixture was diluted to 15 wt. % $ZrO_2$ using THF. The final acrylate-functionalized particles were obtained as a clear, but somewhat hazy, very viscous waxy oil. A small sample of the dry material was spread into a thin film on a glass slide. The nanozirconia-filled material provided a transparent and almost colorless thin film. Based on the mass of zirconia, ligands, and monomers used, the final material contained approximately 60 wt. % zirconia.

Example 8L

Zirconia Particles Functionalized with Isooctyl Acrylate, Acrylic Acid, and 6-(2-biphenoxy)hexyl acrylate (2-BPHA:IOA:AA=0.80:0.18:0.02 wt. fraction)

Based on the general procedure detailed in Example 8C above, acrylate-functionalized nanozirconia was prepared from ligand 1 (17.0 mmol ligand 1), an aqueous solution of acetate-stabilized zirconia (40.0 g sol, 16.49 g $ZrO_2$), ligand 2 (1.34 g, 5.77 mmol), 6-(2-biphenoxy)hexylacrylate (4.17 g, 12.9 mmol), isooctyl acrylate (0.939 g, 5.09 mmol), acrylic acid (0.125 g, 1.73 mmol), and Photoinitiator (0.132 g, 0.589 mmol). The reaction mixture was diluted to 15 wt. % $ZrO_2$ using THF. The final acrylate-functionalized particles were obtained as a clear, but somewhat hazy, yellow, very viscous waxy oil. A small sample of the dry material was spread into a thin film onto a glass slide. The nanozirconia-filled material provided a clear, mostly colorless thin film. Based on the mass of zirconia, ligands, and monomers used, the final material contained approximately 65 wt. % zirconia.

Example 8M

Zirconia Particles Functionalized with Isooctyl Acrylate, Acrylic Acid, and 6-(2-biphenoxy)hexyl acrylate (2-BPHA:IOA:AA=0.80:0.15:0.05 wt. fraction)

Based on the general procedure detailed in Example 8C above, acrylate-functionalized nanozirconia was prepared from ligand 1 (17.3 mmol ligand 1), an aqueous solution of acetate-stabilized zirconia (40.0 g sol, 16.49 g $ZrO_2$), ligand 2 (1.34 g, 5.77 mmol), 6-(2-biphenoxy)hexylacrylate (4.17 g, 12.9 mmol), isooctyl acrylate (0.782 g, 4.24 mmol), acrylic acid (0.261 g, 3.62 mmol), and Photoinitiator (0.132 g, 0.589 mmol). The reaction mixture was diluted to 15 wt. % $ZrO_2$ using THF. The final acrylate-functionalized particles were obtained as a colorless to white foam-like material. A small sample of the dry material was spread into a thin film onto a glass slide. The nanozirconia-filled material provided a clear, mostly colorless thin film. Based on the mass of zirconia, ligands, and monomers used, the final material contained approximately 65 wt. % zirconia.

Example 8N

Zirconia Particles Functionalized with Isooctyl Acrylate, Acrylic Acid, and 6-(2-biphenoxy)hexyl acrylate with Ligand 3 (2-BPHA:IOA:AA=0.80:0.18:0.02 wt. fraction)

One half of the tetrahydrofuran solution of ligand 3 from Example 2 above (47.2 g solution, 15.7 mmol ligand 3) was transferred to a 500 mL round-bottomed flask. An aqueous solution of acetate-stabilized zirconia (36.43 g sol, 14.952 g $ZrO_2$) was added to the tetrahydrofuran solution of ligand 3. The homogeneous solution was allowed to stand for 15 minutes. Then, ligand 2 (1.21 g, 5.23 mmol) was added. The reaction mixture was diluted with tetrahydrofuran (20 mL) and mixed well to provide a somewhat cloudy, but well-dispersed solution. After 20 minutes, the solution of functionalized zirconia nanoparticles was concentrated to dryness in vacuo to provide a white solid. 6-(2-biphenoxy)hexylacrylate (6.40 g, 19.7 mmol), isooctyl acrylate (1.44 g, 7.81 mmol), and acrylic acid (0.160 g, 2.22 mmol) were added. Tetrahydrofuran (~175 mL) was added to provide a 15 wt. % $ZrO_2$ solution. The mixture was sonicated for 30 minutes to provide a well-dispersed, but slightly hazy solution. The solution was transferred to an approximately 500 mL glass bottle. Photoinitiator (0.119 g, 0.531 mmol) was added. The solution was sparged with nitrogen for 30 minutes and then sealed with a TEFLON-lined metal cap, TEFLON tape, and electrical tape. The reaction was placed in front of a lamp ($\lambda$=350 nm) and irradiated while spinning on rollers. After 20 hours, the reaction was opened to air and sampled. $^1$H NMR analysis was consistent with the production of acrylate polymer (>90% conversion). The hazy blue reaction solution was concentrated in vacuo to a clear, but somewhat hazy, very viscous wax-like material. A small sample of the dry material was spread into a thin film onto a glass slide. The nanozirconia-filled material provided a clear, mostly colorless thin film. Based on the mass of zirconia, ligands, and monomers used, the final material contained approximately 55 wt. % zirconia.

Example 8O

Zirconia Particles Functionalized with Isooctyl Acrylate, Acrylic Acid, and 6-(2-biphenoxy)hexyl acrylate with Ligand 3 (2-BPHA:IOA:AA=0.80:0.18:0.02 wt. fraction)

Based on the general procedure detailed in Example 8N, acrylate-functionalized nanozirconia was prepared from ligand 3 (50.0 g solution, 15.7 mmol ligand 3), an aqueous solution of acetate-stabilized zirconia (36.43 g sol, 14.952 g $ZrO_2$), ligand 2 (1.21 g, 5.23 mmol), 6-(2-biphenoxy)hexylacrylate (8.58 g, 26.4 mmol), isooctyl acrylate (1.93 g, 10.5 mmol), acrylic acid (0.214 g, 2.97 mmol), and Photoinitiator (0.119 g, 0.531 mmol). The reaction mixture was diluted to 15 wt. % $ZrO_2$ using THF. The final acrylate-functionalized particles were obtained as a clear, but somewhat hazy, very viscous waxy oil. A small sample of the dry material was spread into a thin film onto a glass slide. The nanozirconia-filled material provided a clear, mostly colorless thin film. Based on the mass of zirconia, ligands, and monomers used, the final material contained approximately 50 wt. % zirconia.

Example 8P

Zirconia Particles Functionalized with Isooctyl Acrylate, Acrylic Acid, and 6-(2-biphenoxy)hexyl acrylate with Ligand 3 (2-BPHA:IOA:AA=0.80:0.18:0.02 wt. fraction)

Based on the general procedure detailed in Example 8N, acrylate-functionalized nanozirconia was prepared from ligand 3 (8.75 mmol ligand 3), an aqueous solution of acetate-stabilized zirconia (36.43 g sol, 14.952 g $ZrO_2$), ligand 2 (1.21 g, 5.23 mmol), 6-(2-biphenoxy)hexylacrylate (8.58 g, 26.4 mmol), isooctyl acrylate (1.93 g, 10.5 mmol), acrylic acid (0.214 g, 2.97 mmol), and Photoinitiator (0.119 g, 0.531 mmol). The reaction mixture was diluted to 15 wt. % $ZrO_2$ using THF. The final acrylate-functionalized particles were obtained as a clear, but somewhat hazy, very viscous waxy oil. A small sample of the dry material was spread into a thin film onto a glass slide. The nanozirconia-filled material provided a clear, mostly colorless thin film. Based on the mass of zirconia, ligands, and monomers used, the final material contained approximately 52 wt. % zirconia.

Example 8Q

Zirconia Particles Functionalized with Isooctyl Acrylate, Acrylic Acid, and 6-(2-biphenoxy)hexyl acrylate with Ligand 3 (2-BPHA:IOA:AA=0.80:0.18:0.02 wt. fraction)

Based on the general procedure detailed in Example 8N, acrylate-functionalized nanozirconia was prepared from ligand 3 (47.2 g solution, 15.7 mmol ligand 3), an aqueous solution of acetate-stabilized zirconia (36.43 g sol, 14.952 g $ZrO_2$), ligand 2 (1.2106 g, 5.23 mmol), 6-(2-biphenoxy)hexylacrylate (4.59 g, 14.1 mmol), isooctyl acrylate (1.03 g, 5.59 mmol), acrylic acid (0.115 g, 1.59 mmol), and Photoinitiator (0.119 g, 0.531 mmol). The reaction mixture was diluted to 15 wt. % $ZrO_2$ using THF. The final acrylate-functionalized particles were obtained as a clear, but somewhat hazy, very viscous waxy oil. A small sample of the dry material was spread into a thin film onto a glass slide. The nanozirconia-filled material provided a clear, mostly colorless thin film. Based on the mass of zirconia, ligands, and monomers used, the final material contained approximately 60 wt. % zirconia.

Thin Films and Adhesives Prepared Containing Functionalized Zirconia Particles

Example 9

Preparation and Testing of Thin Films and Adhesives

Example 9A 2.71 g of acrylate-functionalized nanozirconia from Example 8J was transferred to a 20 mL glass vial. Toluene (1.68 g) was added. The solution was mixed and then sonicated for 10 minutes to provide a well-dispersed, but somewhat hazy solution. A handspread was pulled onto a PE Film using a bar coater. The thin film was dried at 120° C. for 45 minutes. A Release Liner was laminated to the top of the dry film. The adhesive film was 0.0011 inches (0.0028 cm) thick. The 180° peel adhesion was tested on glass and shear strength was tested on stainless steel using the Test Methods described above. The date are presented in Table 3 below.

Examples 9B-9J

The same general procedure for Example 9A was followed. For some of the Examples, a crosslinker (either Flex 10 or XL-353) were added. The data are summarized in Table 3 below.

TABLE 3

| Example | Example Used | Flex 10 (wt. %) | XL-353 (wt. %) | Thickness (cm) | Peel (N/dm) | Shear Strength (min) | Refractive Index (n) |
|---|---|---|---|---|---|---|---|
| 9A | 8J | — | — | 0.0028 | 21 | 16 | 1.6691 |
| 9B | 8J | 0.5 | — | 0.0028 | 40 | 12 | 1.6658 |
| 9C | 8J | 0.8 | — | 0.0028 | 42 | 24 | 1.6678 |
| 9D | 8J | — | 0.5$^a$ | 0.0028 | 22 | 148 | 1.6693 |
| 9E | 8J | — | 0.5$^b$ | 0.0028 | 28 | 46 | 1.6681 |
| 9F | 8J | — | 0.5$^c$ | 0.0025 | 19 | 6 | 1.6694 |
| 9G | 8N | — | — | 0.0033 | 37 | 8 | 1.6595 |
| 9H | 8N | 1 | — | 0.0020 | 47 | 9 | 1.6586 |

TABLE 3-continued

| Example | Example Used | Flex 10 (wt. %) | XL-353 (wt. %) | Thickness (cm) | Peel (N/dm) | Shear Strength (min) | Refractive Index (n) |
|---|---|---|---|---|---|---|---|
| 9I | 8Q | — | — | 0.0030 | <1 | >10,000 | 1.6729 |
| 9J | 8Q | 1 | — | 0.0023 | <1 | >10,000 | 1.6742 |

[a] = irradiated by 350 nm light for 15 minutes;
[b] = irradiated by 350 nm light for 30 minutes;
[c] = not irradiated.

Preparation of Zirconia Particles Functionalized with Polymeric Ligands From Photoinitiator Ligands

Example 10

Zirconia Particles Functionalized with Isooctyl Acrylate with Ligand 5

Ligand 5, prepared in Example 4 (0.0204 g, 0.0577 mmol) was added to a 20 mL glass vial. Next, an aqueous solution of acetate-stabilized zirconia (0.511 g sol, 0.211 g $ZrO_2$) was added followed by tetrahydrofuran (2.0 mL) to produce a heterogeneous mixture containing a white precipitate. Ligand 2 (0.0274 g, 0.118 mmol) was added and the solution was mixed well to provide a homogeneous solution. After standing for 2 hours, a second portion of ligand 2 (0.0275 g, 0.119 mmol) was added followed by tetrahydrofuran (8 mL). The mixture was concentrated in vacuo to a white solid. Tetrahydrofuran (10 mL) was added to resuspend the functionalized particles and the mixture was concentrated in vacuo to a white solid two times. The white solid was then dried in vacuo (~0.01 mm of Hg) for 30 minutes. Tetrahydrofuran (5.5 mL) and a magnetic stir bar were added. The solution was mixed well to provide a homogeneous dispersion. Isooctyl acrylate (0.330 mL, 0.290 g, 1.58 mmol) was added. The solution was sparged with nitrogen for 5 minutes and then sealed with a TEFLON-lined plastic cap, TEFLON tape, and electrical tape. The mixture was irradiated (λ=350 nm) for approximately 19 hours. $^1$H NMR analysis was consistent with the production of polymer and indicated consumption of the acrylate monomer. The reaction mixture was concentrated in vacuo to a clear and colorless oily solid. The product was further dried in vacuo (~0.01 mm of Hg) at 60° C. for 2 days. The absence of solvent was confirmed by $^1$H NMR analysis. The final material contained 35.86% $ZrO_2$ as determined by TGA. The refractive index of the clear and colorless material was 1.5320.

What is claimed is:

1. Surface-modified nanoparticles comprising:
    zirconia nanoparticles; and
    at least one ligand attached to at least one of the zirconia nanoparticles, the ligand comprising:
       a hydroxamate functionality; and
       a reactive group comprising a chain transfer group or a photoinitiator group,
    wherein the ligand comprises the structure:

$R^1N(OH)(CO)$-A-X wherein $R^1$ is selected from a hydrogen atom, an alkyl group, a cycloalkyl group, an aryl group, a heteroaryl group, an aralkyl group, a heteroaryl group, or a heterocycloalkyl group;
    (CO) is a carbonyl group C=O;
    A is a divalent linking group selected from alkylene, arylene, aralkylene, heteroalkylene, heteroarylene, or heteroaralkylene; and
    X is —SH or —(OC)—O—B—O—Ar—(CO)—C(OH)$R^2{}_2$
    wherein B is an alkylene group or arylene group;
    Ar is an aryl or substituted aryl group; and
    each $R^2$ is an alkyl group.

2. The surface-modified nanoparticles of claim 1, wherein the chain transfer group comprises a thiol group.

3. The surface-modified nanoparticles of claim 1, further comprising at least one additional ligand comprising a hydroxamate functionality.

4. The surface-modified nanoparticles of claim 3, wherein the at least one additional ligand comprises the structure:

$R^1N(OH)(CO)$—$R^3$ wherein $R^1$ is selected from a hydrogen atom, an alkyl group, a cycloalkyl group, an aryl group, a heteroaryl group, an aralkyl group, a heteroaryl group, or a heterocycloalkyl group;
    (CO) is a carbonyl group C=O; and
    $R^3$ is an alkyl group, a cycloalkyl group, an aryl group, a heteroaryl group, an aralkyl group, a heteroaryl group, or a heterocycloalkyl group.

5. The surface-modified nanoparticles of claim 3, wherein the at least one additional ligand comprises up to 95% by moles of the total ligands.

6. Surface-modified nanoparticles comprising:
    zirconia nanoparticles; and
    at least one oligomeric ligand attached to at least one of the zirconia nanoparticles, the oligomeric ligand comprising:
       a hydroxamate functionality; and
       an oligomeric group, wherein the oligomeric group is formed by the polymerization of free radically polymerizable monomers,
    wherein the oligomeric group comprises the structure:

$R^1N(OH)(CO)$-A-Z wherein $R^1$ is selected from a hydrogen atom, an alkyl group, a cycloalkyl group, an aryl group, a heteroaryl group, an aralkyl group, a heteroaryl group, or a heterocycloalkyl group;
    (CO) is a carbonyl group C=O;
    A is a divalent linking group selected from alkylene, arylene, aralkylene, heteroalkylene, heteroarylene, or heteroaralkylene; and
    Z is -T-W
    wherein -T- comprises —S— or —(OC)—O—B—O—Ar—(CO)—, wherein
      B is an alkylene group or arylene group; and
      Ar is an aryl or substituted aryl group; and
      W comprises a poly(meth)acrylate or poly(meth)acrylamide group.

7. The surface-modified nanoparticles of claim 6, wherein the free radically polymerizable monomers comprise a (meth)acrylate, a (meth)acrylamide, a vinylic monomer, a styrenic monomer, an alpha-olefin, or a combination thereof.

8. The surface-modified nanoparticles of claim 6, further comprising at least one additional ligand comprising a hydroxamate functionality.

9. The surface-modified nanoparticles of claim 8, wherein the at least one additional ligand comprises the structure:

$R^1N(OH)(CO)$—$R^3$ wherein $R^1$ is selected from a hydrogen atom, an alkyl group, a cycloalkyl group, an aryl group, a heteroaryl group, an aralkyl group, a heteroaryl group, or a heterocycloalkyl group;

(CO) is a carbonyl group C=O; and $R^3$ is an alkyl group, a cycloalkyl group, an aryl group, a heteroaryl group, an aralkyl group, a heteroaryl group, or a heterocycloalkyl group.

10. An article comprising:
a nanoparticle-modified organic matrix, the nanoparticle-modified organic matrix comprising the reaction product of a curable reaction mixture comprising:
at least one free radically polymerizable monomer; and
surface-modified zirconia nanoparticles, wherein the surface-modified zirconia nanoparticles comprise:
zirconia nanoparticles; and
at least one ligand attached to at least one of the zirconia nanoparticles, the ligand comprising:
a hydroxamate functionality; and
a reactive group comprising a chain transfer group or a photoinitiator group,
wherein the at least one ligand comprises the structure:

$R^1N(OH)(CO)$-A-X wherein $R^1$ is selected from a hydrogen atom, an alkyl group, a cycloalkyl group, an aryl group, a heteroaryl group, an aralkyl group, a heteroaryl group, or a heterocycloalkyl group;

(CO) is a carbonyl group C=O;

A is a divalent linking group selected from alkylene, arylene, aralkylene, heteroalkylene, heteroarylene, or heteroaralkylene; and X is —SH or —(OC)—O—B—O—Ar—(CO)—C(OH)$R^2_2$ wherein B is an alkylene group or arylene group;

Ar is an aryl or substituted aryl group; and each $R^2$ is an alkyl group.

11. The article of claim 10, wherein the curable reaction mixture further comprises an initiator.

12. The article of claim 10, wherein the free radically polymerizable monomer comprises at least one monomer selected from a (meth)acrylate, a (meth)acrylamide, a vinylic monomer, a styrenic monomer, an alpha-olefin, or a combination thereof.

13. The article of claim 10, wherein the article comprises an adhesive, a film, a hardcoat, or a dental composition.

14. The article of claim 10, wherein the article is optically clear.

15. A ligand comprising:
a hydroxamate functional group; and
a reactive group comprising a chain transfer group or a photoinitiator group,
wherein the ligand comprises the structure $R^1N(OH)(CO)$-A-X wherein $R^1$ is selected from a hydrogen atom, an alkyl group, a cycloalkyl group, an aryl group, a heteroaryl group, an aralkyl group, a heteroaryl group, or a heterocycloalkyl group;

(CO) is a carbonyl group C=O;

A is a difunctional linking group selected from alkylene, arylene, aralkylene, heteroalkylene, heteroarylene, or heteroaralkylene; and X is —(OC)—O—B—O—Ar—(CO)—C(OH)$R^2_2$ wherein B is an alkylene group or arylene group;

Ar is an aryl or substituted aryl group; and each $R^2$ is an alkyl grow.

16. The ligand of claim 15, wherein the chain transfer group comprises a thiol group.

17. The ligand of claim 15, wherein
$R^1$ is H;
X is —(OC)—O—B—O—Ar—(CO)—C(OH)$R^2_2$
wherein B is an alkylene group with 1-10 carbon atoms;
Ar is a phenylene group;
each $R^2$ is an alkyl group with 1-5 carbon atoms; and
A is an alkylene group with 1-10 carbon atoms.

18. The ligand of claim 17, wherein
B is an ethylene group;
each $R^2$ is a methyl group; and
A is a propylene group.

* * * * *